(12) United States Patent
Knopp et al.

(10) Patent No.: US 10,531,934 B2
(45) Date of Patent: Jan. 14, 2020

(54) SYSTEMS AND METHODS FOR IMPROVED ENGAGEMENT BETWEEN ALIGNERS AND TEETH

(71) Applicant: ALIGN TECHNOLOGY, INC., San Jose, CA (US)

(72) Inventors: Peter G. Knopp, Palo Alto, CA (US); Aaron J. Miller, San Francisco, CA (US); Rob van den Berg, San Ramon, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 209 days.

(21) Appl. No.: 15/197,401

(22) Filed: Jun. 29, 2016

(65) Prior Publication Data
US 2016/0302886 A1   Oct. 20, 2016

Related U.S. Application Data

(60) Division of application No. 13/019,219, filed on Feb. 1, 2011, now Pat. No. 9,408,675, which is a
(Continued)

(51) Int. Cl.
*A61C 7/02* (2006.01)
*A61C 7/00* (2006.01)
(Continued)

(52) U.S. Cl.
CPC ............... *A61C 7/002* (2013.01); *A61C 7/00* (2013.01); *A61C 7/08* (2013.01); *B29C 43/02* (2013.01);
(Continued)

(58) Field of Classification Search
CPC ............................................. A61C 7/00–008
See application file for complete search history.

(56) References Cited

U.S. PATENT DOCUMENTS

| | | | |
|---|---|---|---|
| 2,467,432 A | 4/1949 | Kesling |
| 3,407,500 A | 10/1968 | Kesling |

(Continued)

FOREIGN PATENT DOCUMENTS

| | | | |
|---|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.
(Continued)

*Primary Examiner* — Yogesh P Patel
(74) *Attorney, Agent, or Firm* — Wilson Sonsini Goodrich & Rosati

(57) ABSTRACT

A system and method for repositioning teeth in a patient jaw includes an attachment bonded to a tooth. The attachment has at least one force receiving component for receiving a force. A polymeric shell repositioning appliance is positioned over at least some of the teeth in the patient jaw. The polymeric shell has at least one force transmitting component for engaging the force receiving component to form a locus of engagement. The locus of engagement transmits the force and moves but is maintained as the tooth is repositioned. In specific embodiments the locus of engagement is maintained over a substantial range of motion. The force transmitted at the locus of engagement increases in response to the tooth lagging an intended position. A space between the positioned appliance and the tooth permits the tooth to move into an intended position.

7 Claims, 25 Drawing Sheets

Related U.S. Application Data continuation of application No. 10/958,710, filed on Oct. 4, 2004, now Pat. No. 7,901,207, which is a continuation of application No. 10/126,105, filed on Apr. 18, 2002, now Pat. No. 6,830,450.

(51) Int. Cl.
*A61C 7/08* (2006.01)
*B33Y 10/00* (2015.01)
*B33Y 50/02* (2015.01)
*B33Y 80/00* (2015.01)
*B29C 43/02* (2006.01)
*B29C 43/56* (2006.01)
*B33Y 50/00* (2015.01)
*B29L 31/00* (2006.01)

(52) U.S. Cl.
CPC .............. *B29C 43/56* (2013.01); *B33Y 10/00* (2014.12); *B33Y 50/02* (2014.12); *B33Y 80/00* (2014.12); *B29C 2043/561* (2013.01); *B29L 2031/753* (2013.01); *B33Y 50/00* (2014.12)

(56) References Cited

U.S. PATENT DOCUMENTS

| | | |
|---|---|---|
| 3,600,808 A | 8/1971 | James |
| 3,660,900 A | 5/1972 | Lawrence |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,020,556 A | 5/1977 | Sotman |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A * | 4/1991 | Lemchen .................. A61C 7/12 433/229 |
| 5,017,133 A | 5/1991 | Miura |
| 5,022,855 A | 6/1991 | Jeckel |
| 5,027,281 A | 6/1991 | Rekow et al. |
| 5,035,613 A | 7/1991 | Breads et al. |
| 5,049,077 A | 9/1991 | Goldin et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,536,168 A | 7/1996 | Bourke |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,300 A | 3/1997 | Tepper |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,683,244 A | 11/1997 | Truax |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |

(56) References Cited

U.S. PATENT DOCUMENTS

| | | | |
|---|---|---|---|
| 5,975,893 | A | 11/1999 | Chishti et al. |
| 5,978,893 | A * | 11/1999 | Bakshi .................... G11C 8/12 |
| | | | 365/230.03 |
| 6,015,289 | A | 1/2000 | Andreiko et al. |
| 6,044,309 | A | 3/2000 | Honda |
| 6,049,743 | A | 4/2000 | Baba |
| 6,062,861 | A | 5/2000 | Andersson |
| 6,068,482 | A | 5/2000 | Snow |
| 6,099,314 | A | 8/2000 | Kopelman et al. |
| 6,123,544 | A * | 9/2000 | Cleary .................... A61C 7/146 |
| | | | 433/24 |
| 6,152,731 | A | 11/2000 | Jordan et al. |
| 6,183,248 | B1 * | 2/2001 | Chishti .................... A61C 7/00 |
| | | | 433/6 |
| 6,190,165 | B1 | 2/2001 | Andreiko et al. |
| 6,217,325 | B1 | 4/2001 | Chishti et al. |
| 6,217,334 | B1 | 4/2001 | Hultgren |
| 6,227,850 | B1 | 5/2001 | Chishti et al. |
| 6,244,861 | B1 | 6/2001 | Andreiko et al. |
| 6,257,882 | B1 | 7/2001 | Wyllie, II |
| 6,276,930 | B1 | 8/2001 | Pozzi |
| 6,293,790 | B1 | 9/2001 | Hilliard |
| 6,299,440 | B1 | 10/2001 | Phan et al. |
| 6,309,215 | B1 * | 10/2001 | Phan ........................ A61C 7/00 |
| | | | 433/24 |
| 6,315,553 | B1 | 11/2001 | Sachdeva et al. |
| 6,322,359 | B1 | 11/2001 | Jordan et al. |
| 6,350,120 | B1 | 2/2002 | Sachdeva et al. |
| 6,382,975 | B1 | 5/2002 | Poirier |
| 6,398,548 | B1 | 6/2002 | Muhammad et al. |
| 6,402,707 | B1 | 6/2002 | Ernst |
| 6,431,870 | B1 * | 8/2002 | Sachdeva ................ A61C 7/00 |
| | | | 433/213 |
| 6,482,298 | B1 | 11/2002 | Bhatnagar |
| 6,524,101 | B1 | 2/2003 | Phan et al. |
| 6,554,611 | B2 | 4/2003 | Shishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 6,830,450 | B2 * | 12/2004 | Knopp .................... A61C 7/00 |
| | | | 433/18 |
| 7,901,207 | B2 | 3/2011 | Knopp et al. |
| 9,408,675 | B2 | 8/2016 | Knopp et al. |
| 2002/0006597 | A1 | 1/2002 | Andreiko et al. |
| 2002/0064759 | A1 | 5/2002 | Durbin et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2011/0123944 | A1 | 5/2011 | Knopp et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1108397 A1 | 6/2001 |
| ES | 463897 A1 | 1/1980 |
| FR | 2369828 A1 | 6/1978 |
| FR | 2652256 A1 | 3/1991 |
| GB | 1550777 A | 8/1979 |
| GB | 15500777 | 8/1979 |
| JP | S5358191 A | 5/1978 |
| JP | H0428359 A | 1/1992 |
| JP | 08508174 | 9/1996 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Andrews, The Six Keys to Optimal Occlusion Straight Wire, Chapter 3, pp. 13-24 (No Date Given).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty, NATO Symposium on Applications of Human Biostereometrics," Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

(56) References Cited

OTHER PUBLICATIONS

Biostar Opeation & Training Manual. Great Lakes Orthodontics, Ltd. 199 Fire Tower Drive, Tonawanda, New York. 14150-5890, 20 pages total (1990).
Biostar Opeation & Training Manual. Great Lakes Orthodontics, Ltd. 199 Fire Tower Drive, Tonawanda, New York. 14150-5890, 20 pages total (No Date Given).
Blu, et al., "Linear interpolation revitalized", IEEE Trans. Image Proc., 13(5):710-719 (May 2004).
Boughton, B., Invisible Force, ConactPoint, University of the Pacific School of Dentistry, San Francisco, California, 80(3) pp. 21-24 (2000).
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision," Part 3 The Computer Gives New Vision—Literally,"Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.

Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dentrac Corporation, Dentrac document, pp. 4-13 (No Date Given).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
DuraClearTM product information, Allesee Orthodontic Appliances-Pro Lab, 1 page (No Date Given).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Friedman (Ed.) Technology Forum, Compendium:22(2), (Feb. 2001).
Futterling et a/., "Automated Finite Element Modeling of a Human Mandible with Dental Implants," JS WSCG '98-Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et a/., "Computer-Based Image Analysis of Artificial Root Surface Caries, Abstracts of Papers," J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).

(56) References Cited

OTHER PUBLICATIONS

Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www. essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et a/., "CAD/CAM for Dental Restorations—Some of the Curious Challenges," IEEE Trans. Biomed. Eng., 38(4):344-345 (Apr. 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.

(56) References Cited

OTHER PUBLICATIONS

Siemens, "CEREC—Computer-Reconstruction," High Tech in der Zahnmedizin, 14 pages total (2004).
Siemens, "CEREC—Computer-Reconstruction," High Tech in der Zahnmedizin, 14 pages total (No Date Given).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
Tru-Tain Orthodontic & Dental Supplies, Product Brochure, Rochester, Minnesota 55902, 16 pages total (No Date Given).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances-Pro Lab product information for patients, 2 pages (2002).
You May Be a Candidate for This Invisible No-Braces Treatment, Allesee Orthodontic Appliances-Pro Lab product information for patients, 2 pages (No Date Given).
Co-pending U.S. Appl. No. 16/375,651, filed Apr. 4, 2019.

\* cited by examiner

SYSTEMS AND METHODS FOR IMPROVED ENGAGEMENT BETWEEN ALIGNERS AND TEETH

CROSS-REFERENCES TO RELATED APPLICATIONS

The present application is a divisional of U.S. patent application Ser. No. 13/019,219, filed Feb. 1, 2011, now U.S. Pat. No. 9,408,675, issued Aug. 9, 2016 which is a continuation of U.S. patent application Ser. No. 10/958,710, filed Oct. 4, 2004, now U.S. Pat. No. 7,901,207, issued Mar. 8, 2011, which is a continuation of U.S. patent application Ser. No. 10/126,105, filed Apr. 18, 2002, now U.S. Pat. No. 6,830,450, issued Dec. 14, 2004, the full disclosures of which are incorporated herein by reference.

BACKGROUND OF THE INVENTION

The present invention is related generally to the field of orthodontics. More particularly, the present invention is related to improved systems and methods for removably attaching a dental positioning appliance to the dental features of a patient during orthodontic treatment.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and 0-rings. The brackets and bands are bonded to the patient's teeth using a suitable material, such as dental adhesive. Once the adhesive has set, the archwire is attached to the brackets by way of slots in the brackets. The archwire links the brackets together and exerts forces on them to move the teeth over time. Twisted wires or elastomeric 0-rings are commonly used to reinforce attachment of the arch wire to the brackets. Attachment of the arch wire to the brackets is known in the art of orthodontia as "ligation" and wires used in this procedure are called "ligatures." The elastomeric 0-rings are called "plastics."

After the archwire is in place, periodic meetings with the orthodontist are required, during which the patient's braces will be adjusted. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontist's office. Moreover, from a patient's perspective, they are unsightly and uncomfortable. Moreover, the archwire and ligatures which connect the brackets in a continuous network make brushing, flossing between the teeth and other dental hygiene procedures difficult, possibly contributing to the development of gingivitis. Consequently, alternative orthodontic treatments are needed. In particular, it would be desirable to use appliances which can be removed by the patient during daily dental hygiene routines, while participating in athletic activities, or for cosmetic purposes.

A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations to a final desired configuration. A full description of an exemplary elastic polymeric positioning appliance is described in U.S. Pat. No. 5,975,893, and in published PCT Publication No. WO 98/58596 which designates the United States and which is assigned to the assignee of the present invention. Both documents are incorporated by reference for all purposes.

In addition to their ease of use, polymeric positioning appliances are generally transparent, providing an improved cosmetic appearance, and impart substantial force on the teeth, due to stiffness of the appliance. The stiffness of an elastic positioning appliance is a result of the modulus of the thermoformable polymer materials from which it is made. The higher the modulus of the materials, the higher the stiffness of the appliance. When a patient positions such an appliance over a prescribed group of teeth, one or more of the teeth will provide a base or attachment region for holding the positioning appliance in place while the stiffness of the polymeric material will impart a resilient repositioning force against one or a portion of the remaining teeth. By designing the appliance to cover the teeth, a much larger contact surface area is afforded compared to traditional spring retainers and wire-based appliances. However, such attaching and repositioning abilities of removable elastic positioning appliances are still dependent on the physical features and configuration of the patient's teeth, palette, and previous dental work, to name a few. For example, shell-like elastic polymeric positioning appliances have difficulty applying certain forces to individual teeth, such as extrusive force (e.g. pulling or raising a tooth relative to the jaw).

Attachment devices anchored to one or several teeth can improve repositioning of the teeth with polymeric appliances. Particularly difficult tooth movements are rotations and extrusions. Using appliances with attachment devices can improve tooth rotation and extrusion. However, during treatment, coupling between an appliance and attachment may become disengaged. This disengagement may occur if a tooth does not move as planned, or moves in a planned direction but not as rapidly as planned. If the planned position of the tooth and attachment differs from the actual position of the tooth and attachment, the receptacle for the attachment formed in the polymeric shell may not properly receive the attachment on the tooth. If the receptacle formed in the polymeric shell does not properly receive the attachment, the force applied to the tooth decreases and the treatment outcome may be less than ideal.

Thus, it would be desirable to provide tooth positioners, systems, and methods which apply adequate force in desired directions to selected teeth at specific times during treatment. In particular, it would be desirable to enable the fabrication and use of removable positioners and systems which can apply extrusive, rotational, and other directional forces which have heretofore been difficult to apply with removable positioners. It would also be desirable to reduce the cost of the orthodontic treatment and retain the patient benefits of a removable appliance in cases where they might not otherwise be available. At least some of these objectives will be met by the designs and methods of the present invention described hereinafter.

BRIEF SUMMARY OF THE INVENTION

The present invention provides improved methods and systems for using removable polymeric shell appliances for moving teeth. In particular, the present invention configures and positions a force receiving component on a tooth attachment, typically an anchor bonded to a tooth, and a force applying component on the shell appliance, typically a receptacle formed in a wall of the shell which receives the attachment when the shell is placed over the teeth. The attachment and receptacle will be configured to create an engagement point or region therebetween, where the engagement point or region moves or "shifts" as the teeth are repositioned so that the force transmitted is optimized to promote efficient tooth movement throughout the treatment stage using each particular appliance. In one example, both the force applying and the force receiving surfaces are inclined planes which slide over each other as the tooth is moved so that a desired force is maintained on the tooth. In another example, the further receiving and applying surfaces comprise pawl-and-ratchet structures that permit relative positional adjustment as the tooth is moved. Other examples are described hereinafter.

In a first aspect the invention comprises a method of repositioning teeth. The method comprises bonding an attachment having at least one force receiving component to a preselected position on at least one of the teeth. A provided shell repositioning appliance has at least one force transmitting component for transmitting a force. The polymeric shell repositioning appliance is placeable over the teeth so that the force transmitting component and the force receiving component engage each other at a contact point. The contact point is within a locus of engagement, and a position of the contact point adjusts within the locus of engagement as the tooth is repositioned.

In specific embodiments, the locus of engagement extends over a pre-selected distance. The force receiving component and the force transmitting component are positioned so that the force transmitted to at least one tooth which lags its intended position is increased. The polymeric shell appliance placed over the teeth may include a cavity shaped so that a space between the appliance and the tooth permits the tooth to move into an intended position. The polymeric shell and attachment may be shaped to permit the attachment to move relative to the appliance along a channel as the contact point adjusts position within the locus of engagement. In some embodiments a first pair comprises the force transmitting component and a second pair comprises force receiving component, and each member of each pair are positioned on opposing sides of the tooth.

In many embodiments the pre-selected distance over which the locus of engagement extends is at least about 0.5 mm. The distance may be at least about 1 mm. The force transmitting component and force receiving component may be arranged to rotate at least one of the teeth with the transmitted force. In some embodiments the force transmitting component and force receiving component are arranged to extrude at least one of the teeth with the transmitted force. Alternatively, the force transmitting component and force receiving component may be arranged to intrude at least one of the teeth with the force. The force transmitting component and the force-receiving component may comprise a cam and a follower. In some embodiments the contact point adjusts position within the locus of engagement, and this adjustment establishes an equilibrium as the force transmitted to the at least one tooth which lags its intended position is increased.

The force transmitting and force receiving components may be arranged to counter a force from a first surface with a force from a second surface. In specific embodiments the force from the first surface is an intrusive force and the force from the second surface is an extrusive force. Alternatively, the force from the first surface is an extrusive force and the force from the second surface is an intrusive force. A single attachment device may include a first surface and a second surface that counters a force from the first surface. Alternatively, a first attachment device may comprise the first surface and a second attachment device may comprise the second surface. In specific embodiments, the force transmitting component and the force-receiving component comprise a pawl and a ratchet. The force-transmitting component may comprise the ratchet and the force-receiving component may comprise the pawl. Alternatively, the force-transmitting component may include the pawl and the force-receiving component may include the ratchet. In specific embodiments the force-receiving component and the force-transmitting component comprise meshing teeth.

In another aspect the invention comprises a system for repositioning teeth in a patient jaw comprising an attachment for bonding to a tooth at a pre-selected position. The attachment has at least one force receiving component for receiving a force. The system also includes a polymeric shell repositioning appliance placeable over at least some of the teeth in the patient jaw. The appliance has at least one force transmitting component positioned to engage the force receiving component of the attachment when the attachment and the force receiving component engage each other at a contact point. The contact point adjusts a contact position within the locus of engagement as the tooth is repositioned.

In some embodiments the locus of engagement extends over a preselected distance. The force receiving component and the force transmitting component are positioned so that the force transmitted to at least one tooth which lags its intended position is increased. In some embodiments the polymeric shell appliance placed over the teeth includes a cavity shaped so that a space between the appliance and the tooth permits the tooth to move into an intended position. The polymeric shell and attachment are shaped to permit the attachment to move relative to the appliance along a channel as the contact point adjusts position within the locus of engagement. A pair may comprise the force transmitting component and the force receiving component, each member of each pair may be on opposing sides of the tooth.

In many embodiments the pre-selected distance over which the locus of engagement extends is at least about 0.5 mm. The distance may be at least about 1 mm. The force transmitting component and the force receiving component maybe arranged to rotate at least one of the teeth with the force. Alternatively, the force transmitting component and the force receiving component may be arranged to intrude at least one of the teeth with the force. The force transmitting component and the force receiving component may be arranged to extrude at least one of the teeth with the force. The contact point may adjust position within the locus of engagement to establish an equilibrium as the force transmitted to the at least one tooth which lags its intended position is increased.

In some embodiments the force transmitting and force receiving components are arranged to counter a force from a first surface with a force from a second surface. In specific embodiments, the force from the first surface is an intrusive force and the force from the second surface is an extrusive force. Alternatively, the force from the first surface is an extrusive force and the force from the second surface is an intrusive force. A single attachment device may comprise the first surface and the second surface. Alternatively, a first attachment device may comprise the first surface and a second attachment device comprises the second surface.

In further embodiments the force transmitting component and the force-receiving component comprise a pawl and a ratchet. In specific embodiments the force-transmitting component comprises the ratchet and the force-receiving component comprises the pawl. Alternatively, the force-transmitting component comprises the pawl and the force-receiving component comprises the ratchet. In an embodiment, the force receiving component and the force-transmitting component comprise meshing teeth.

In yet another aspect the invention comprises a method for designing a polymeric shell tooth repositioning appliance. The method includes locating an attachment on at least one tooth among several teeth of a model to define at least one force receiving component for receiving a transmitted force. The method also includes positioning an attachment receptacle to define at least one force transmitting component in a polymeric shell placeable over the teeth. The force transmitting and force receiving components are shaped to engage each other at a contact point within a locus of engagement. A position of the contact point adjusts within the locus of engagement as the tooth is repositioned.

In specific embodiments the locus of engagement extends over a preselected distance. The force receiving component and the force transmitting component are positioned so that the force transmitted to at least one tooth which lags its intended position is increased. The polymeric shell appliance placed over the teeth may include a cavity shaped so that a space between the appliance and the tooth permits the tooth to move into an intended position. The polymeric shell and attachment are shaped to permit the attachment to move relative to the appliance along a channel as the contact point adjusts its position within the locus of engagement. A prominence may be placed at the locus of engagement to increase the transmitted force.

In some embodiments the model is a computer model and the attachment is a virtual attachment. Modifying the virtual attachment forms a modified virtual attachment. The modified virtual attachment may be for forming the attachment receptacle in the polymeric shell. The modifying of the virtual attachment may include modifying a position of the virtual attachment. The modified virtual attachment may be similar to a shape of at least a portion of the virtual attachment, for example a similar shape formed by truncating a portion of the virtual attachment. In preferred embodiments, the modifying of the virtual attachment increases the force transmitted by the polymeric shell. The modifying of the virtual attachment may include enhancing a surface detail of the virtual attachment to form a modified virtual attachment having enhanced surface detail.

DETAILED DESCRIPTION OF THE INVENTION

Figure 1A:
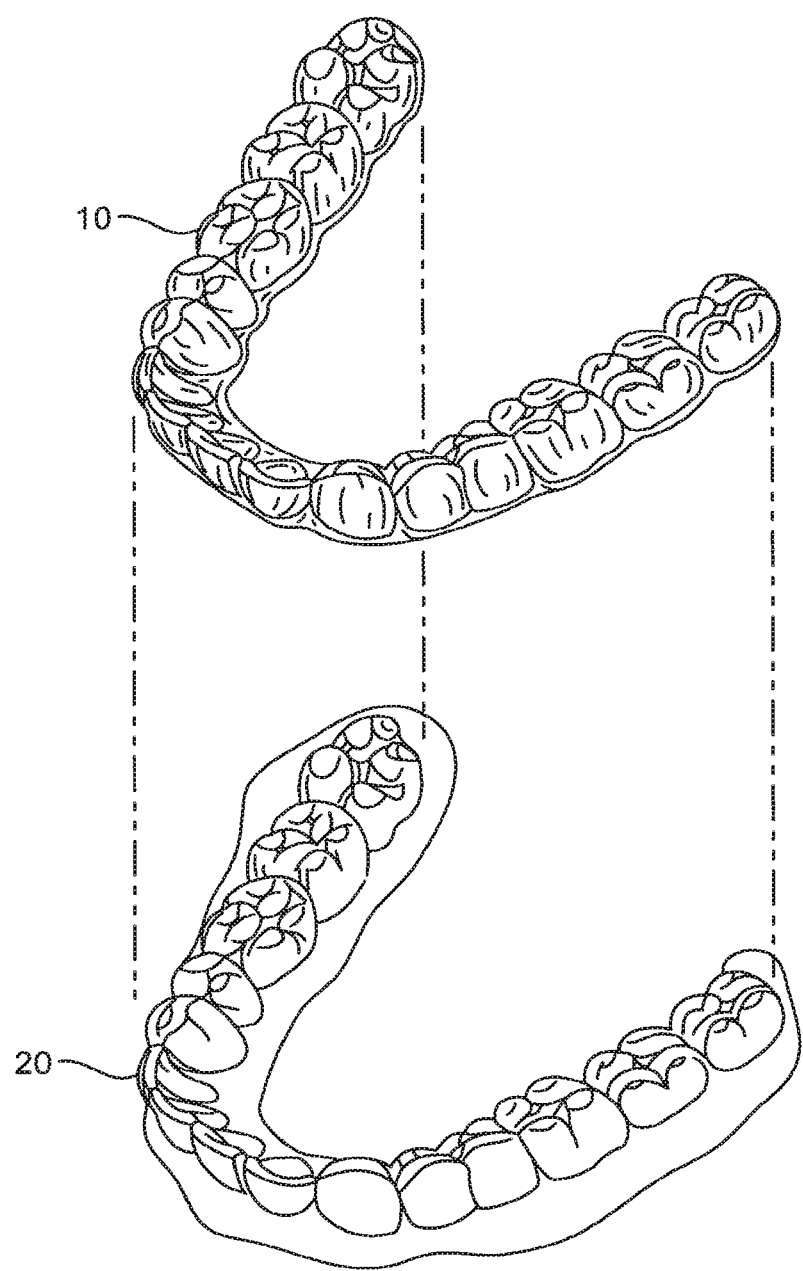
FIG. 1A illustrates an appliance for incorporating the present invention positioned above a set of teeth.

The present invention provides improved systems and methods for moving teeth by positioning appliances over teeth. Appliances are often referred to as aligners. An appliance 10 and a set of teeth 20 are illustrated in FIG. 1A. Specific systems and methods for producing the appliances are described in U.S. Pat. No. 5,975,893, the full disclosure of which is incorporated herein by reference. The teeth are bonded to attachment devices to effect rotation, translation, intrusion and extrusion of the teeth. Attachment devices and appliances for incorporating the present invention are described in U.S. Pat. No. 6,309,215, the full disclosure of which is incorporated herein by reference. A series of appliances are positioned over the teeth and attachments to reposition teeth from an initial position to a final position. Interactions of the attachment devices and appliances include cam and follower, meshing gear, and ratchet and pawl type interactions. The interactions of the present invention deliver force to a tooth over a range of motion, thereby providing an improved engagement between the appliance and tooth. This engagement is maintained if a tooth lags an intended position during treatment.

Each appliance is designed to incrementally move each treated tooth to an intended position. When an appliance is first positioned over the teeth, a treated tooth typically is not located at the intended position prescribed by the geometry of the appliance. In other words, the treated tooth position lags the intended position. For example, if a previous appliance has treated a tooth and the position of the treated tooth has moved to the intended position prescribed by the previous appliance, the treated tooth position will lag the intended position prescribed by a new appliance. The intended position will lag the actual position by the incremental motion intended between the previous and new appliances. If prior appliances have intended motion of a tooth, the tooth may not have achieved an intended position from a previous appliance. In this case the position of the position of the tooth will lag the intended position of the current appliance by more than the intended incremental motion between appliances. Incremental motion of an intended position of a treated tooth between sequential appliances is typically between about 0.1 and 1.0 mm, preferably between about 0.2 and 0.6 mm and more preferably between about 0.25 and 0.5 mm.

Each appliance is designed to incrementally move each treated tooth to an intended position. When an appliance is first positioned over the teeth, a treated tooth typically is not located at the intended position prescribed by the geometry of the appliance. In other words, the treated tooth position lags the intended position. For example, if a previous appliance has treated a tooth and the position of the treated tooth has moved to the intended position prescribed by the previous appliance, the treated tooth position will lag the intended position prescribed by a new appliance. The intended position will lag the actual position by the incremental motion intended between the previous and new appliances. If prior appliances have intended motion of a tooth, the tooth may not have achieved an intended position from a previous appliance. In this case the position of the position of the tooth will lag the intended position of the current appliance by more than the intended incremental motion between appliances. Incremental motion of an intended position of a treated tooth between sequential appliances is typically between about 0.1 and 1.0 mm, preferably between about 0.2 and 0.6 mm and more preferably between about 0.25 and 0.5 mm.

The present invention has the advantage of engaging a lagging tooth by employing a movable locus of engagement. The movable locus of engagement typically has a range of engagement permitting engagement between the appliance and attachment even if the treated tooth position lags the intended tooth position by a distance greater than the intended incremental motion of the tooth between sequential appliances. A space in the appliance is provided for the tooth to move into an intended position, and a channel in the appliance permits the attachment to move along the locus of engagement as described in more detail herein below. As used herein, a locus of engagement having a substantial range of motion encompasses a locus of engagement having a range of motion greater than a distance of an intended incremental motion of a tooth treated by an appliance. A range of movement of a locus of engagement is typically between about 0.1 and 4.0 mm, preferably between about 0.2 and 2 mm, and more preferably between about 0.5 and 1.5 mm.

A patient's teeth are repositioned from an initial tooth arrangement to a final tooth arrangement by placing a series of incremental position adjustment appliances in the patient's mouth. Conveniently, the appliances are not affixed and the patient may place and replace the appliances at any time during the procedure. The first appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the patient's mouth, where the final appliance has a geometry selected to progressively reposition teeth from the last intermediate arrangement to the final tooth arrangement.

The polymeric appliance 10 of FIG. 1A is preferably formed from a thin sheet of a suitable elastomeric polymeric, such as Tru-Tain 0.03 in. thermal forming dental material, Tru-Tain Plastics, Rochester, Minn. 55902. Usually, no wires or other means will be provided for holding the appliance in place over the teeth. In accord with an aspect of the present invention, it will be desirable or necessary to provide individual attachments on teeth with corresponding receptacles in the appliance 10 so that the appliance can apply a force on the tooth which would generally not be possible in the absence of such an attachment.

The methods incorporating the present invention will generally rely on manipulating an initial digital data set (IDDS) at a computer or workstation having a suitable graphical user interface (GUI) and software appropriate for viewing and modifying the images. The IDDS is obtained from digitized measurements of the teeth. While some embodiments incorporating the present invention will rely on computer manipulation of digital data, the systems of the present invention comprising multiple dental appliances having incrementally differing geometries may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described in the patent literature, using pressure and vacuum molding techniques. While such manual creation of the appliance systems of the present invention will generally be much less preferred, systems so produced will come within the scope of the present invention.

Figure 1B:
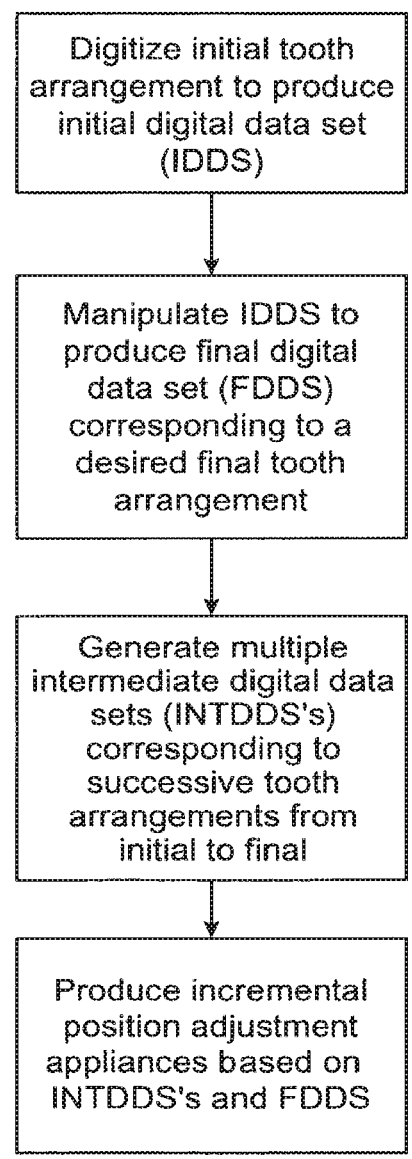
FIG. 1B illustrates a method of generating digital data sets for incorporating the present invention.

Referring to FIG. 1B, after the IDDS has been obtained, the digital information will be introduced to the computer or other workstation for manipulation. In one approach, individual teeth and other components will be "cut" to permit their individual repositioning or removal from the digital data. After thus "freeing" the components, the user will often follow a prescription or other written specification provided by the treating professional. Alternatively, the user may reposition them based on the visual appearance or using rules and algorithms programmed into the computer. Once the user is satisfied with the final arrangement, the final tooth arrangement is incorporated into a final digital data set (FDDS).

Based on both the IDDS and the FDDS, a plurality of intermediate digital data sets (INTDDS's) are generated to correspond to successive intermediate tooth arrangements. The system of incremental position adjustment appliances can then be fabricated based on the INTDDS's.

Figure 1C:
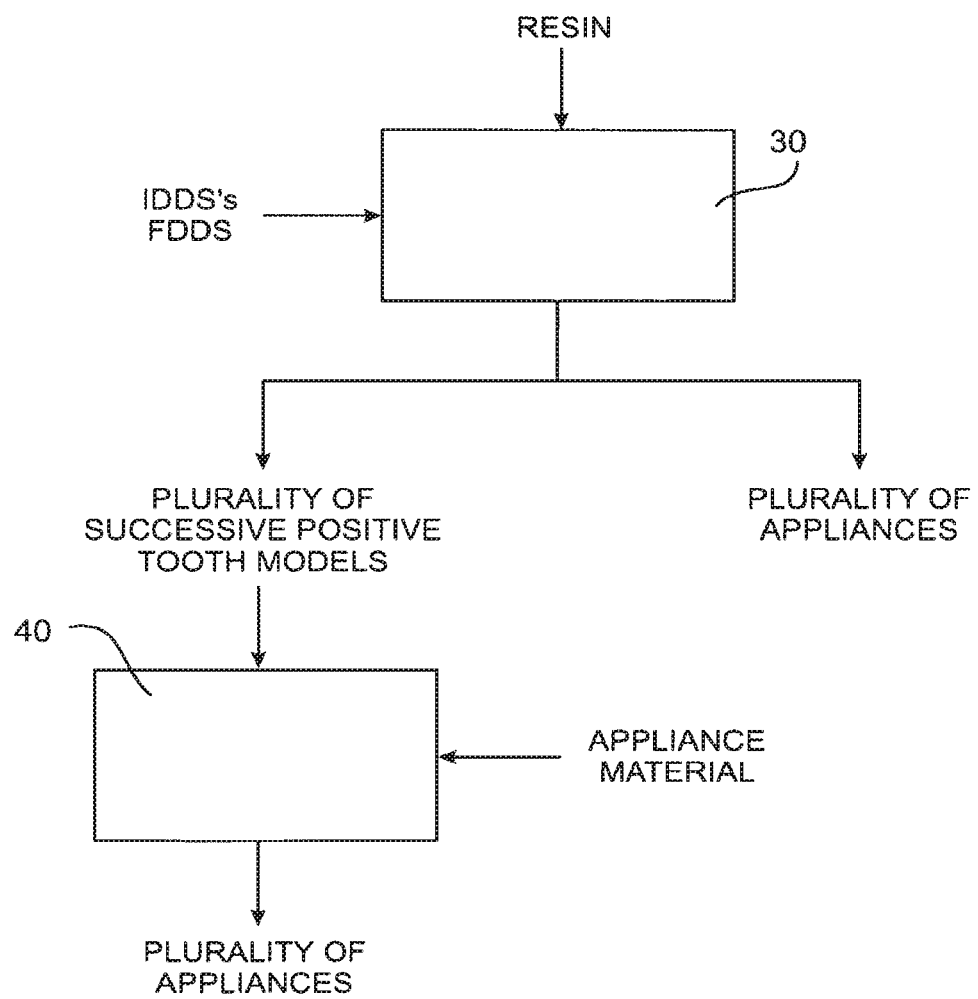
FIG. 1C illustrates alternative processes for producing a plurality of appliances utilizing digital data sets incorporating the present invention and representing the intermediate and final appliance designs.

Once the intermediate and final data sets have been created, the appliances may be fabricated as illustrated in FIG. 1C. Preferably, fabrication methods will employ a rapid prototyping device 30 such as a stereo lithography machine. A particularly suitable rapid prototyping machine is Model SLA-250/50 available from 3D System, Valencia, Calif. The rapid prototyping machine 30 will selectively harden a liquid or other non-hardened resin into a three-dimensional structure which can be separated from the remaining non-hardened resin, washed, and used either directly as the appliance or indirectly as a mold for producing the appliance. The prototyping machine 30 will receive the individual digital data sets and produce one structure corresponding to each of the desired appliances. Generally, because the rapid proto typing machine 30 may utilize a resin having non-optimum mechanical properties and which may not be generally acceptable for patient use, it will be preferred to use the prototyping machine to produce molds which are, in effect, positive tooth models of each successive stage of the treatment. After the positive models are prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under BIOSTAR™ from Great Lakes Orthodontics, Ltd., Tonawanda, N.Y. 14150. The molding machine 40 produces each of the appliances directly from the positive tooth model and the desired material. Suitable vacuum molding machines are available from Raintree Essix, Inc.

Figure 1D:
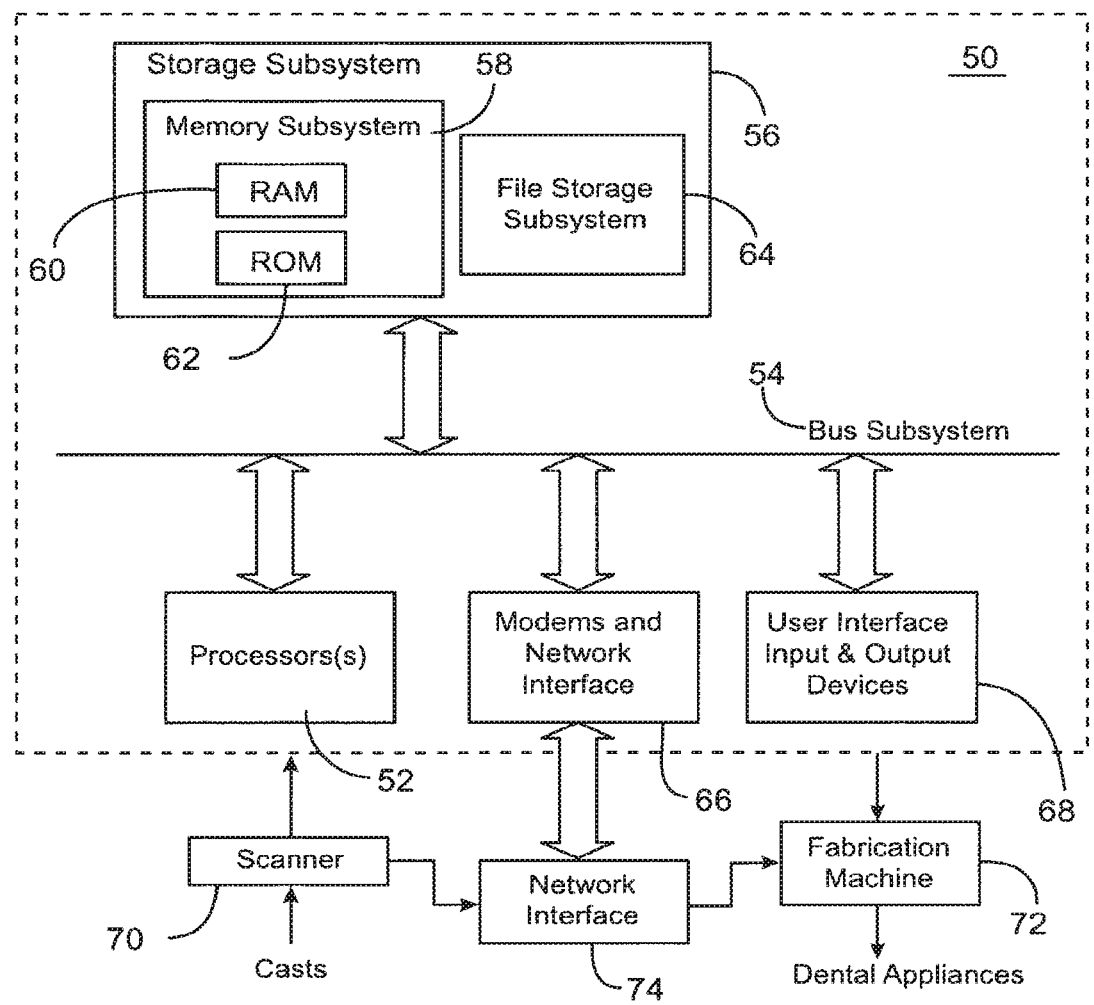
FIG. 1D illustrates a computer system for incorporating an aspect of the present invention.
Figure 1E:
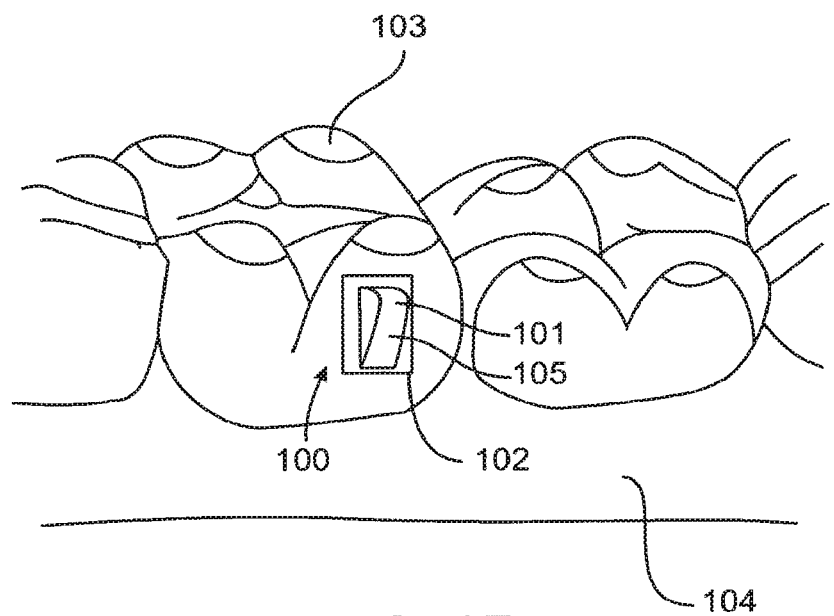
FIG. 1E illustrates a patient's tooth having an attachment device for incorporating the present invention.

A simplified block diagram of a data processing system 50 is illustrated in FIG. 1D. Data processing system 50 typically includes at least one processor 52 which communicates with a number of peripheral devices over bus subsystem 54. These peripheral devices typically include a storage subsystem 56 (memory subsystem 58 and file storage subsystem 64), a set of user interface input and output devices 68, and an interface to outside networks 66, including the public switched telephone network. This interface is shown schematically as "Modems and Network Interface" block 66, and is coupled to corresponding interface devices in other data processing systems over communication network interface 74. Data processing system 50 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 56 maintains the basic programming and data constructs that provide the functionality of the present invention. The software modules discussed above are typically stored in storage subsystem 56. Storage subsystem 56 typically comprises memory subsystem 58 and file storage subsystem 64.

Memory subsystem 58 typically includes a number of memories including a main random access memory (RAM) 60 for storage of instructions and data during program execution and a read only memory (ROM) 62 in which fixed instructions are stored. In the case of Macintosh-compatible personal computers the ROM would include portions of the operating system; in the case of IBM-compatible personal computers, this would include the BIOS (basic input/output system).

File storage subsystem 64 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by SYQUEST and others, and flexible disk cartridges, such as those marketed by IOMEGA. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines Similarly, the input devices and display need not be at the same location as the processor.

Bus subsystem 54 is shown schematically as a single bus, but a typical system has a number of buses such as a local bus and one or more expansion buses, as well as serial and parallel ports. Network connections are usually established through a device such as a network adapter on one of these expansion buses or a modem on a serial port. The client computer may be a desktop system or a portable system.

Scanner 70 is responsible for scanning casts of the patient's teeth obtained either from the patient or from an orthodontist and providing the scanned digital data set information to data processing system 50 for further processing. In a distributed environment, scanner 70 may be located at a remote location and communicate scanned digital data set information to data processing system 50 over network interface 74.

Fabrication machine 72 fabricates dental appliances based on intermediate and final data set information received from data processing system 50. In a distributed environment, fabrication machine 72 may be located at a remote location and receive data set information from data processing system 50 over network interface 74.

Referring to FIG. IE, an embodiment of an attachment device 100 is shown bonded to a tooth 103 above gingiva 104. The attachment device 100 may be comprised of an attachment body 101 having a base 102, which may be integral or separate and permanently or removable joined. The attachment device 100 includes a surface 105 for engaging an appliance to form a movable locus of engagement. The movable locus of engagement permits relative motion between the appliance and attachment and transmits force from the appliance to the attachment and tooth over a range of motion.

Figure 2:
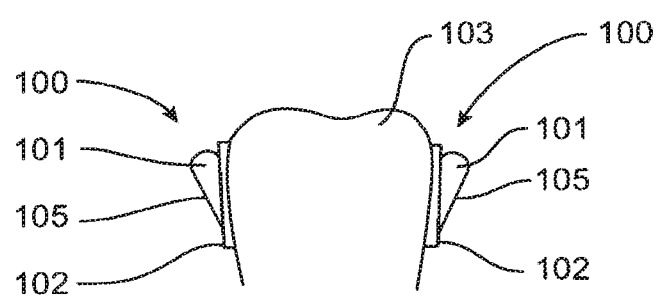
FIG. 2 illustrates a mesial view of a pair of exemplary attachment devices for extruding a tooth in accord with an aspect of the present invention.
Figure 3:
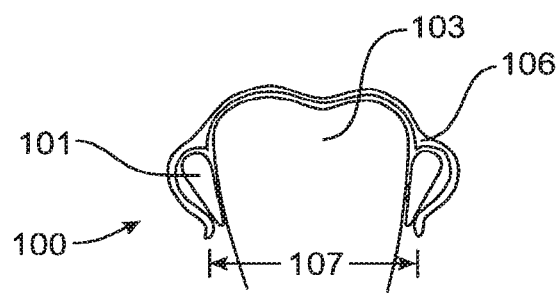
FIG. 3 illustrates a mesial view of a pair of attachment devices as in FIG. 2 covered by an appliance with a tooth in an intended position.
Figure 4:
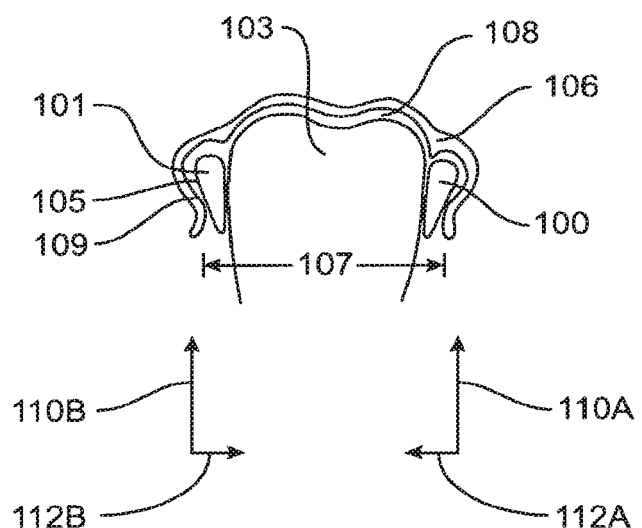
FIG. 4 illustrates a mesial view of appliance engaging a pair of attachment devices in a manner similar to a cam and follower in response to the tooth lagging an intended position.
Figure 4A:
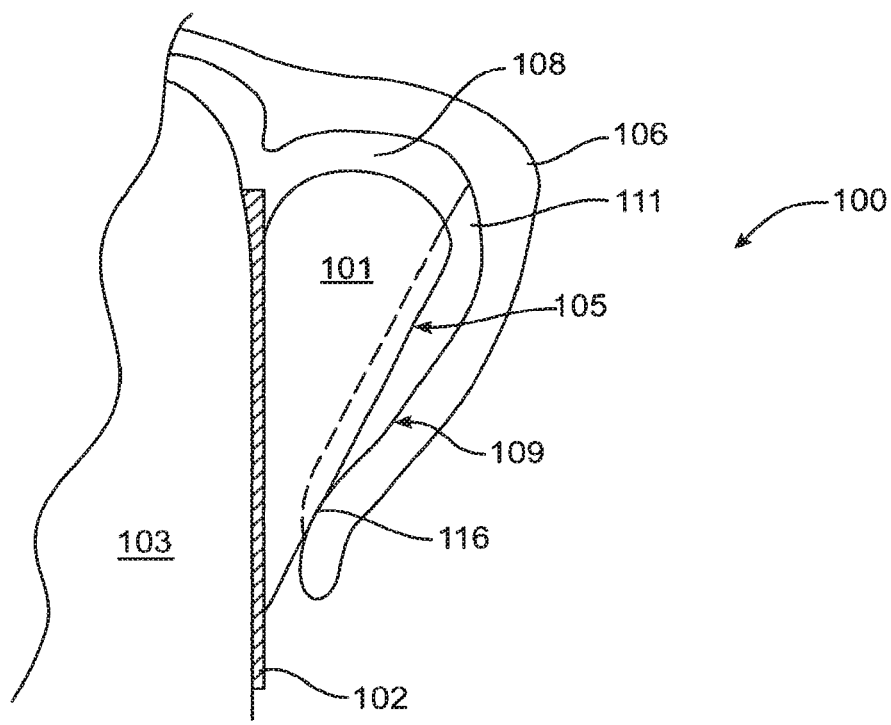
FIG. 4A illustrates an enlarged mesial view of an attachment device covered by an appliance as in FIG. 4.
Figure 4B:
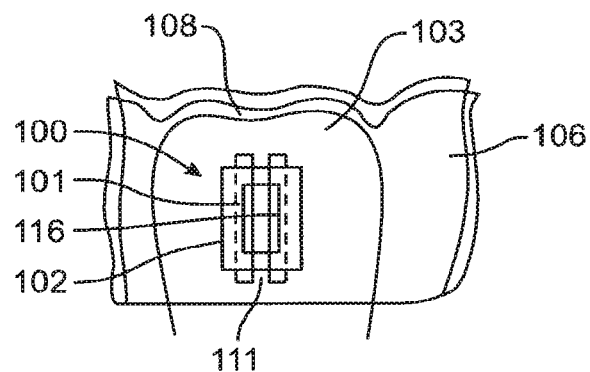
FIG. 4B illustrates a buccal view of an attachment device as in FIG. 4.

A pair of attachment devices 100 illustrated in FIG. 2 is for extruding a tooth 103. An appliance 106 positioned over a tooth 103 and attachments 100 are illustrated in FIG. 3. As illustrated in FIG. 3, the tooth is at an intended position. During treatment of the tooth, a position of the tooth lags an intended position as illustrated in FIGS. 4 and 4A and as described above. A surface 105 of a body 101 of an attachment 100 engages a surface 109 of the appliance 106. The engagement of surface 105 of attachment 100 with surface 109 of appliance 106 forms a movable locus of engagement 116 at a contact point or contact region. As used herein a contact point encompasses a localized region of contact between a surface 109 of an appliance 106 and a surface 105 of an attachment 100. A locus of engagement 116 is maintained during relative motion of tooth 103 to appliance 106. A buccal view of an attachment device as in FIG. 4 is illustrated in FIG. 4B. A channel Ill formed in appliance 106 permits a locus of engagement 116 to be maintained over a substantial range of motion. A space 108 permits tooth 103 to move into an intended position. In an alternate embodiment a channel is formed in a body 101 of attachment 100.

A dimension 107 across the appliance 106 increases, thereby stretching appliance 106 and increasing forces applied to tooth 103 as illustrated by arrows 110A, 110B, 112A and 112B. The opposing positions of the pair of attachment devices 100 cancel the horizontal applied forces 112A and 112B. The resulting extruding force applied to the tooth is the sum of forces 110A and 110B. A space 108 permits the tooth to advance in response to the applied forces 110A and 110B. An increasing prominence of surface 105 as tooth 103 deviates from an intended position increases stretching deformation of appliance 106 across dimension 107. Forces applied to tooth 103 increase in response to tooth 103 deviating from an intended position. This increase in force in response to an increased error in the actual tooth position relative to the intended position provides corrective movement of tooth 103.

An intended position of a treated tooth is prescribed in an appliance geometry for the treated tooth. The attachment body 101 follows a path of motion prescribed by the surface 109 of appliance 106. The surface 109 of appliance 106 follows the motion prescribed by the attachment 100 which acts a cam. A series of sequential appliances may be used to provide an increased motion of attachment 100 and tooth 103.

The appliance positioned over the tooth is a force transmitting component which applies force to the force receiving attachment devices that in turn transfer the received force to the tooth. The force transmitting and force receiving components are a force couple. Increasing deformation of appliance 106 increases the force transmitted from the appliance to the attachment and tooth. As a tooth increasingly lags an intended position, deformation of the appliance and the force transmitted to the tooth via an attachment increases. As described above, the tooth moves in response to the forces applied to the tooth. As the tooth lags an intended position, forces applied to the tooth increase, and as the tooth advances toward and intended position, forces applied to the tooth decrease. Equilibrium Movement ceases when equilibrium is established between the forces applied and transmitted to the tooth and the position achieved by the tooth.

Figure 4C:
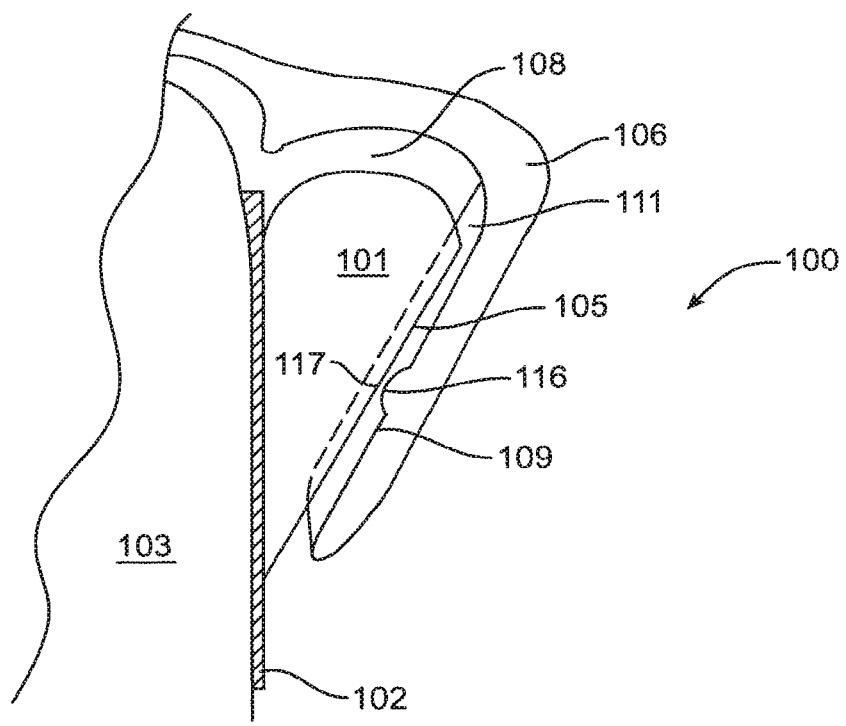
FIG. 4C illustrates a mesial view of an alternate cam and follower embodiment in which the appliance includes a prominence for increasing a force applied to the attachment and tooth.
Figure 5A:
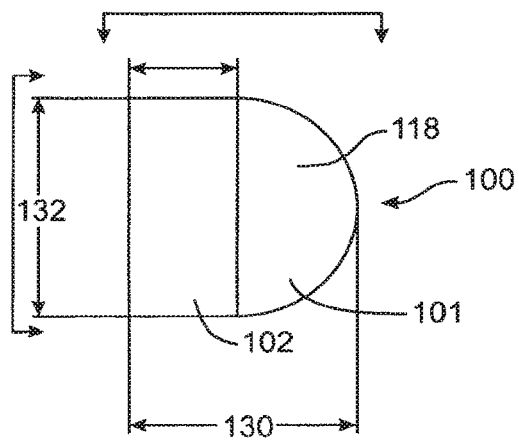
FIGS. 5A-D illustrate views of an exemplary attachment device for bonding to a tooth for intruding or extruding the tooth.
Figure 5B:
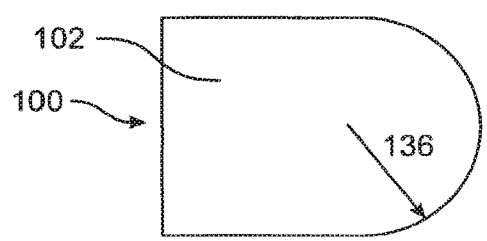
Figure 5C:
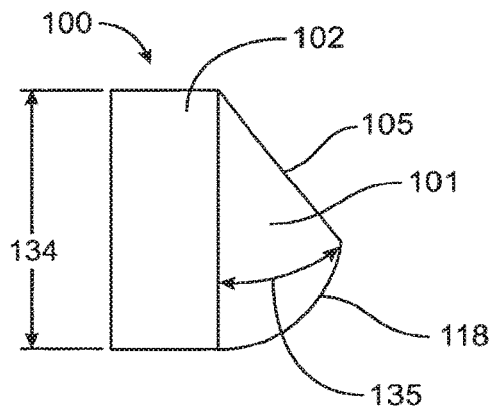
Figure 5D:
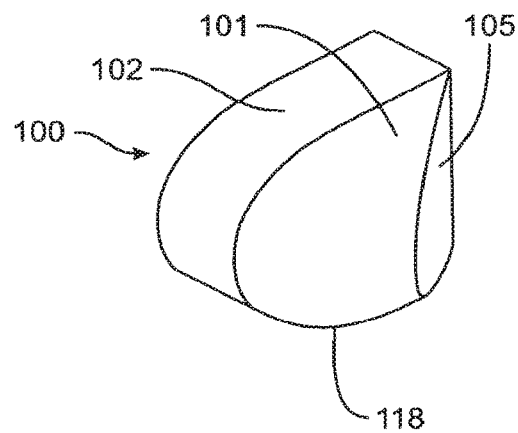

A mesial view of an alternate cam and follower embodiment is illustrated in FIG. 4C. The appliance includes a prominence 117, or pressure point, at locus of engagement 116 for increasing a force applied to the attachment and tooth.

Figure 5:
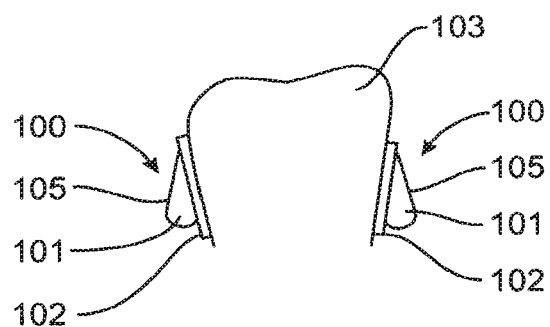
FIG. 5 illustrates a mesial view of a pair of attachment devices bonded to a tooth that are for intruding the tooth.

As illustrated in FIG. 5, an embodiment of the invention uses a pair of wedge shaped attachments 100 for intruding a tooth 103. An appliance has a surface for engaging the attachments to form a moving locus of engagement as described above. The moving locus of engagement exerts an intruding force on the tooth.

Referring to FIGS. 5A-5D, an exemplary embodiment of a wedge shaped attachment 100 has a surface 105 for engaging the appliance, a transition surface 118, and a base 102. Front, side, top and isometric views of the exemplary embodiment are illustrated in FIGS. 5A-5D respectively. Transition surface 118 provides a smooth transition from surface 105 to base 102 and also permits a size of base 102 to increase thereby providing improved bonding to tooth 103. Height 130, length 134 and width 132 of attachment 100 are varied to desirably reposition tooth 103 without interfering with teeth or lingual or labial surfaces of the mouth. Also, the size of base 102 does not exceed a size of exposed tooth for bonding base 102. A length 134 of attachment 100 is typically between 2 and 6 mm and preferably between 3 and 5 mm. A width 132 of attachment 100 is typically between 1 and 4 mm and preferably between 2 and 3 mm. An angle of inclination 135 of surface 105 is also varied to desirably reposition tooth 103. The angle of inclination 135 is typically between 10 and 60 degrees, preferably between 20 and 50 degrees and more preferably between 30 and 40 degrees. A radius of curvature 136 of attachment base 102 may also be varied, and is typically half of the width 132 of attachment device 100. Transition surface 118 varies to provide a smooth transition between base 102 and inclined surface 105.

Figure 6A:
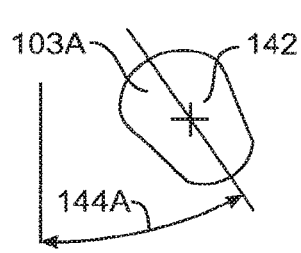
FIGS. 6A-G illustrate a method of rotating a tooth in accord with an aspect of the present invention.
Figure 6B:
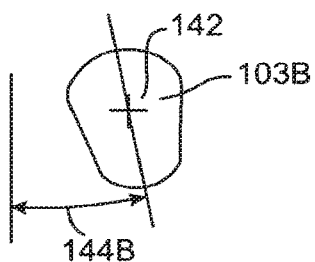
Figure 6C:
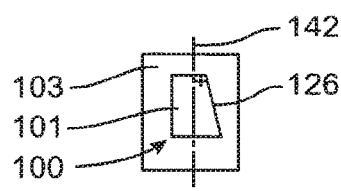
Figure 6D:
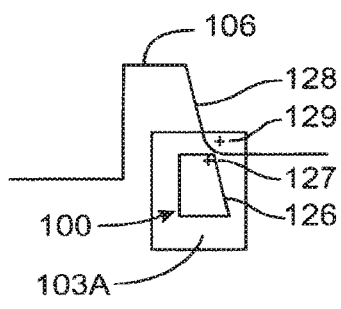
Figure 6E:
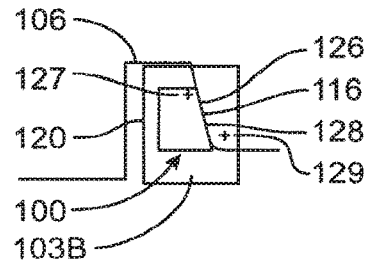
Figure 6F:
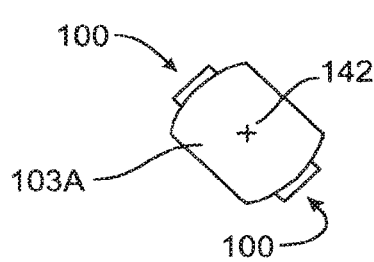
Figure 6G:
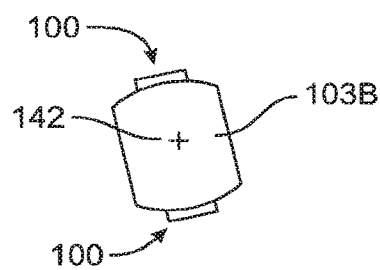

Referring to FIGS. 6A-6G in which a method of rotating a tooth is illustrated, an initial tooth 103A at rotation angle 144A is illustrated in FIG. 6A. An intended rotated tooth 103B at rotation angle 144B is illustrated in FIG. 6B. An attachment 100 having a body 101 with an inclined surface 126 is positioned on a tooth 103 relative to an intended axis of rotation 142 as illustrated in FIG. 6C and FIG. 6F. An appliance 106 is positioned near initial tooth 103A as illustrated in FIG. 6D. A portion 129 of surface 128 of appliance 106 is positioned near a portion 127 of surface 126 of attachment 100. The surface 128 of appliance 106 engages and slides along surface 126 of attachment device 100 and forms locus of engagement 116 as illustrated in FIG. 6E. Follower surface 128 of appliance 106 drives the motion of surface 126 on attachment 100 and tooth 103 and drives tooth and attachment toward an equilibrium as described above. The portion 129 of surface 128 of appliance 106 slides over portion 127 of surface 126 of attachment 100. The rotated tooth 103B is driven toward equilibrium between the force transmitted by the surface 128 of appliance 106 and the force received by the surface 126 of attachment 100. A space 120 permits the tooth to move into an intended position and extends a range of motion of locus of engagement 116. The rotated tooth 103B in a final intended position rotated about axis of rotation 142 is illustrated in FIG. 6G. Rotation of tooth from an initial tooth 103A position to a rotated tooth 103B position may be achieved with several appliances 106.

Figure 7:
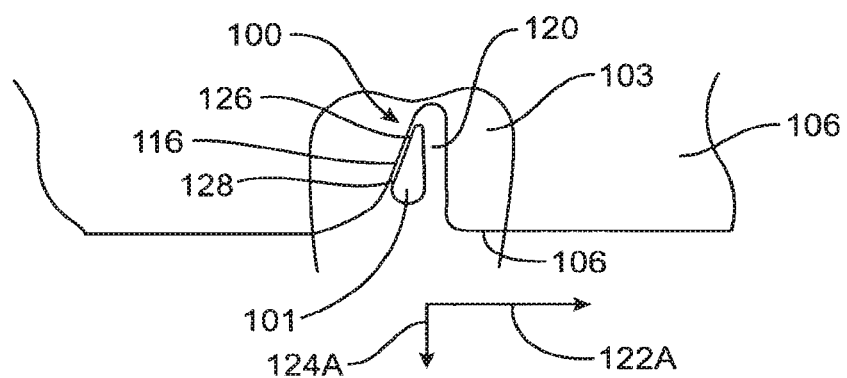
FIG. 7 illustrates a buccal view of an embodiment of the present invention comprising an attachment device and appliance for rotating a tooth in response to occlusal gingival motion of an engaging surface of the appliance.
Figure 7A:
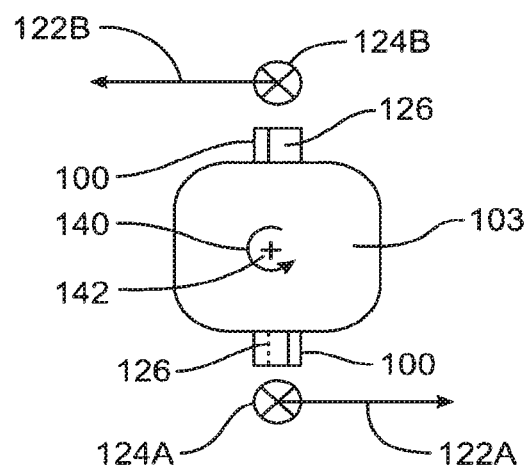
FIG. 7A illustrates an occlusal view of a pair of attachment devices for rotating a tooth as in FIG. 7.

Referring to FIG. 7 an embodiment of an attachment 100 for rotating a tooth 103 by an engaging appliance 106 is illustrated. Rotation of tooth 103 occurs in response to occlusal-gingival motion of a surface 128 of appliance 106. Attachment 100 has a body 101 having a sloped surface 126 that engages a surface 128 of appliance 106. The engagement of a surface 128 of appliance 106 with a surface 126 of attachment 100 forms a movable locus of engagement 116. A space 120 permits the tooth to move into an intended position and extends a range of motion of locus of engagement 116. The force transmitted from the appliance to the attachment and tooth has a rotational component 122A and an intrusive component 124A. As illustrated in FIG. 7A, a pair of attachments 100 provide forces 122A and 122B that form a force couple for rotating 140 tooth 103 about an axis of rotation 142. An angle of inclination of surface 126 encompasses an angle measured with reference to the occlusal-gingival direction, or vertical direction as seen in FIG. 7. An angle of inclination of the surface 126 of attachment 100 is between about 5 and 60 degrees. Preferably an angle of inclination is between about 10 and 40 degrees.

Figure 8:
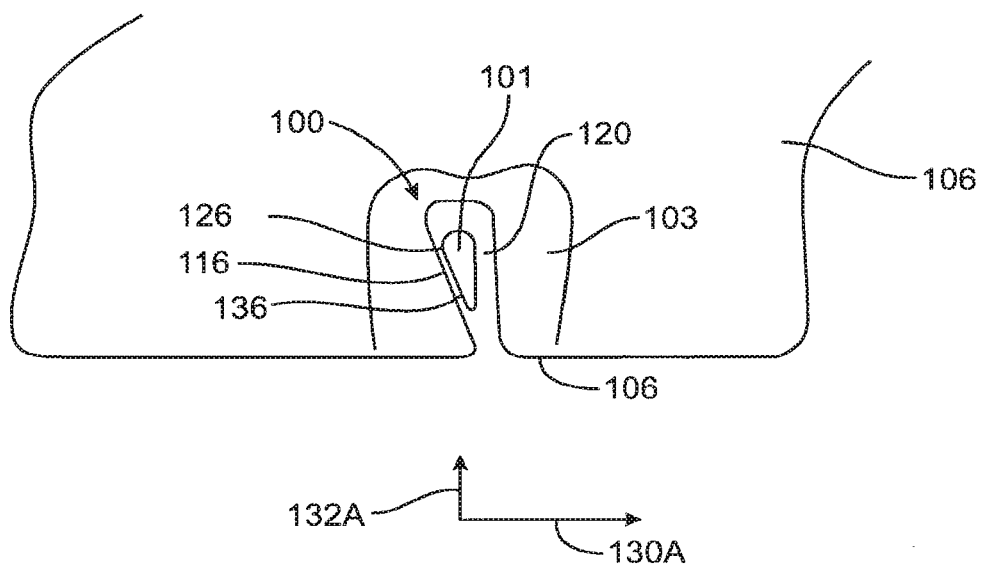
FIG. 8 illustrates a buccal view of an embodiment of the present invention comprising an attachment device and appliance for rotating a tooth in response to gingival occlusal motion of an engaging surface of the appliance.
Figure 8A:
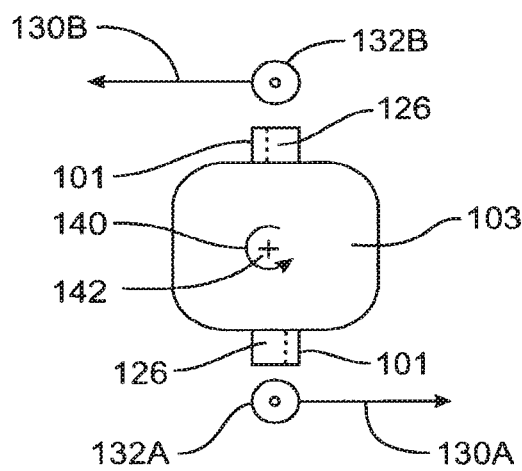
FIG. 8A illustrates an occlusal view of a pair of attachment devices for rotating a tooth as in FIG. 8.

Referring to FIG. 8 an alternate embodiment of an attachment 100 for rotating a tooth 103 by engaging an appliance 106 is illustrated. Rotation of tooth 103 occurs in response to gingival-occlusal motion of a surface 136 of appliance 106. Attachment 100 has a body 101 having a sloped surface 126 that engages a surface 136 of appliance 106. The engagement of a surface 136 of appliance 106 with a surface 126 of attachment 100 forms a movable locus of engagement 116. A space 120 permits the tooth to move into an intended position and extends a range of motion of locus of engagement 116. The force transmitted from the appliance to the attachment has a rotational component 130A and extrusive force component 132A. As illustrated in FIG. 8A, a pair of attachments 100 provide forces 130A and 130B that form a force couple for rotating 140 tooth 103 about an axis of rotation 142.

Figure 9:
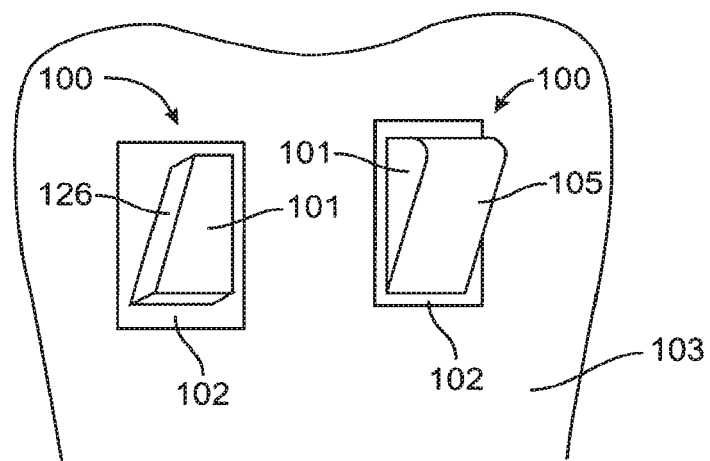
FIG. 9 illustrates a buccal view of an embodiment of the present invention comprising a pair of attachment devices for rotating the tooth by generating a rotational force from a first attachment that also generates a slight intrusive force, and a second attachment for countering the intrusive force with an extrusive force from a surface of the second attachment.

Referring to FIG. 9 illustrating a buccal view of a pair of attachment devices bonded to a side of a tooth 103, attachments 100 include surfaces 105 and 126. Surface 126 rotates tooth 103 and produces a slight intrusive force as described above. Surface 105 produces an extrusive force on tooth I 03 as described above. The extrusive force of surface 105 counters the slight intrusive force of surface 126 while surface 126 rotates tooth 103.

Figure 10:
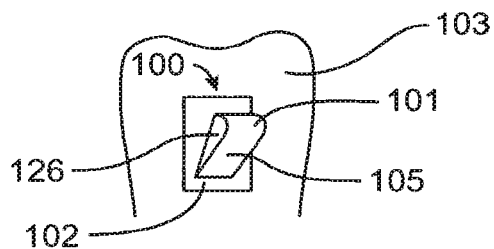
FIG. 10 illustrates a buccal view of an installed attachment device having a surface for rotating the tooth and a surface for extruding the tooth to counter an intrusive force of the surface for rotating the tooth.
Figure 10A:
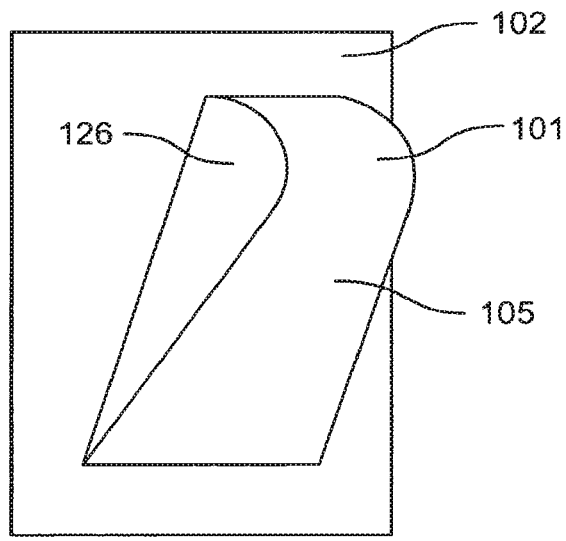
FIG. 10A illustrates an enlarged view of an attachment device as in FIG. 10.
Figure 11A:
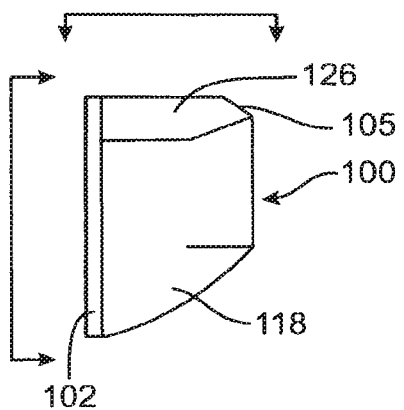
FIGS. 11A-D illustrate views of an exemplary attachment device for rotating a tooth that has a surface for rotating the tooth, a surface for extruding the tooth in response to a slight intrusion force from the surface for rotating, and a smooth transition surface for gently tapering the slopes of surfaces.
Figure 11B:
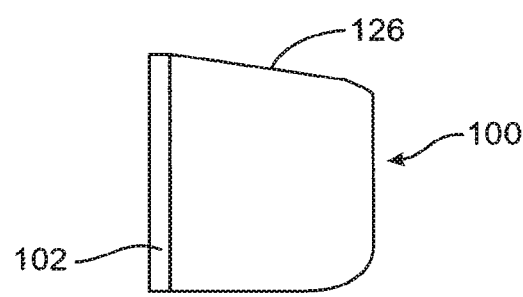
Figure 11C:
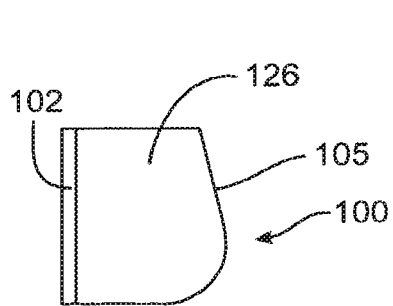
Figure 11D:
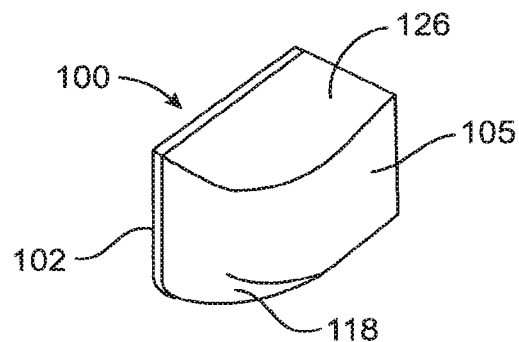

A buccal view of an installed attachment device is illustrated in FIG. 10. A surface 126 for rotating a tooth 103 and a surface 105 for extruding a tooth are combined as a single attachment 100. An enlarged view of an attachment device as in FIG. 10 is illustrated in FIG. 10A.

An exemplary attachment device 100 for rotating a tooth is illustrated in FIGS. 11A-D. A surface 126 for rotating a tooth and a surface 105 for extruding a tooth are combined as a single attachment device 100. Attachment device 100 also includes a transition surface 118. Transition surface 118 provides a gentle transition between surfaces 105 and 126 and base 102. Transition surface 118 permits base 102 to be enlarged while providing a smooth transition between surfaces 105 and 126. In practice it may be desirable to increase a size of base 102 to increase an area of bonding between base 102 and an exposed surface of a tooth.

Figure 12A:
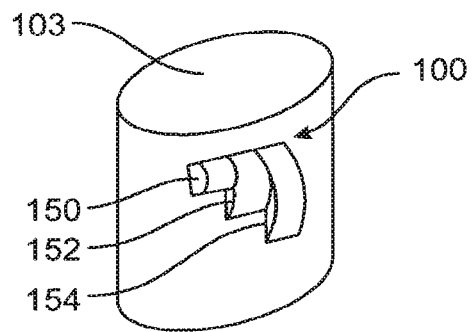
FIG. 12A illustrates several abutting attachment devices mounted to a tooth for altering force directions over time.

Several abutting attachment devices 100 mounted to a tooth 103 are illustrated in FIG. 12A. Individual attachment devices 150, 152 and 154 provide an alteration of force directions over time. An appliance engages an appropriate attachment device for transmitting a desired force to a tooth.

Figure 12B:
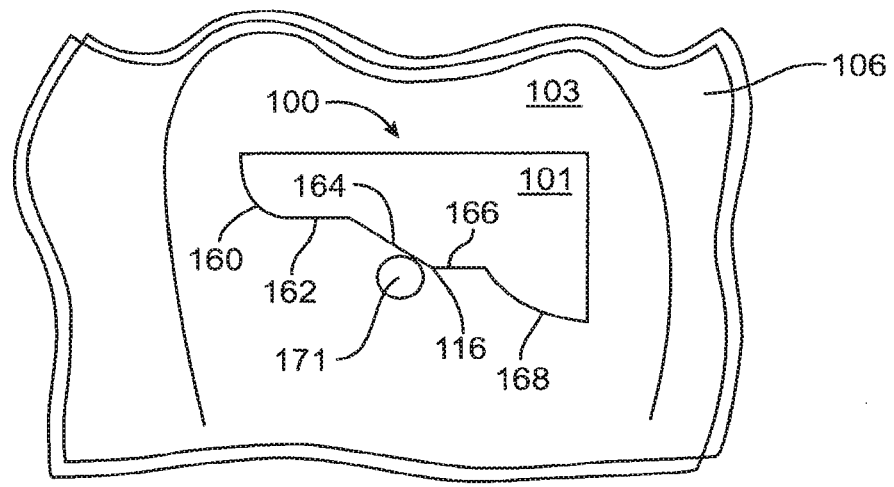
FIG. 12B illustrates an attachment device mounted to a tooth and providing several surfaces to engage a surface of the appliance.

An alternate embodiment of an attachment device 100 mounted to a tooth 103 and providing several surfaces 160, 162, 164, 166 and 168 to engage a surface of an appliance is illustrated in FIG. 12B. The attachment 100 includes curved surfaces 160 and 168, flat surfaces 162 and 166 and sloped surface 164. An appliance 106 controls motion of an attachment 100 that follows a path of motion prescribed by a sequence of sequential appliances 106. The appliance 106 includes a follower 171. The follower 171 engages a surface 164 of attachment 100 to form a locus of engagement 116. During the course of treatment, the follower 171 and locus of engagement 116 move along surfaces 160, 162, 164, 166 and 168 with subsequent appliances. The moving locus of engagement 116 extrudes tooth 103. In alternate embodiments tooth 103 is intruded by the force transmitted by the appliance at the moving locus of engagement. In a further embodiment, the attachment includes a single round surface and the appliance includes several surfaces for engaging the attachment.

Figure 12C:
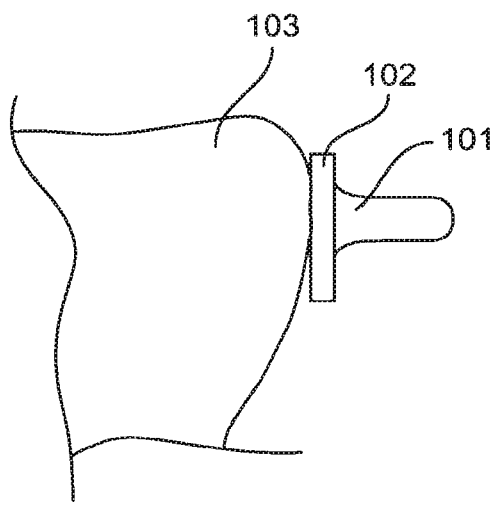
FIGS. 12C and 12D illustrate an attachment device for following a surface of an appliance.
Figure 12D:
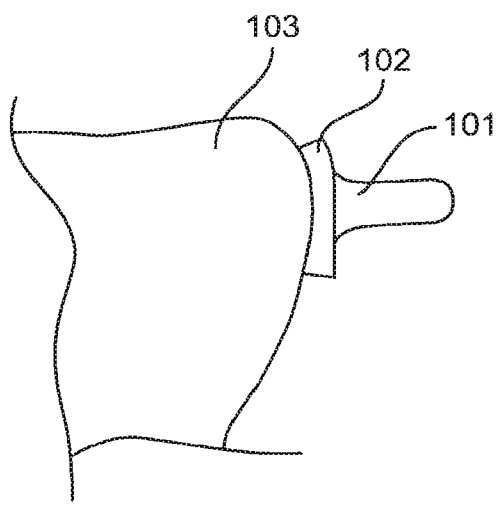

Attachment devices using a body 101 having a singe round surface to engage an appliance are illustrated in FIGS. 12C and D. A base 102 of an attachment is flat as illustrated in FIG. 12C and curved to match a tooth 103 as illustrated in FIG. 12D.

Figure 12E:
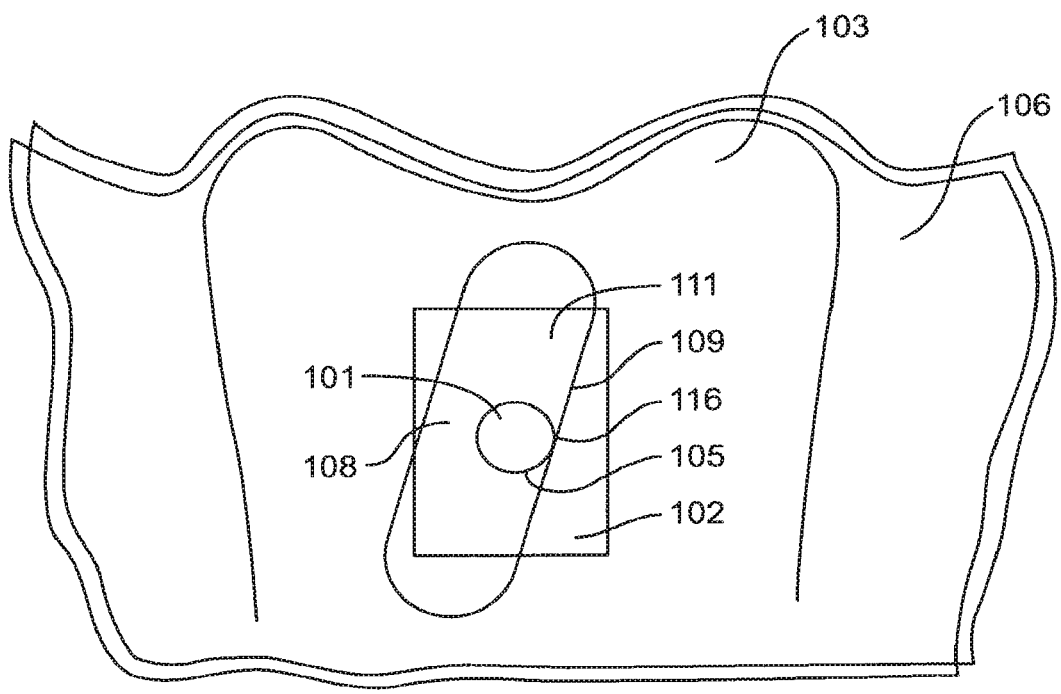
FIG. 12E illustrates an appliance for rotating a tooth and an attachment as in either of FIGS. 12C and 12D.

A round attachment device as described above is used to rotate a tooth in an embodiment of the present invention illustrated in FIG. 12E. Engaging a surface 109 of an appliance 106 with a surface 105 of an attachment body 101 forms a locus of engagement 116. A pair of attachments and an appliance are used to rotate the tooth 103 as described above.

Figure 13A:
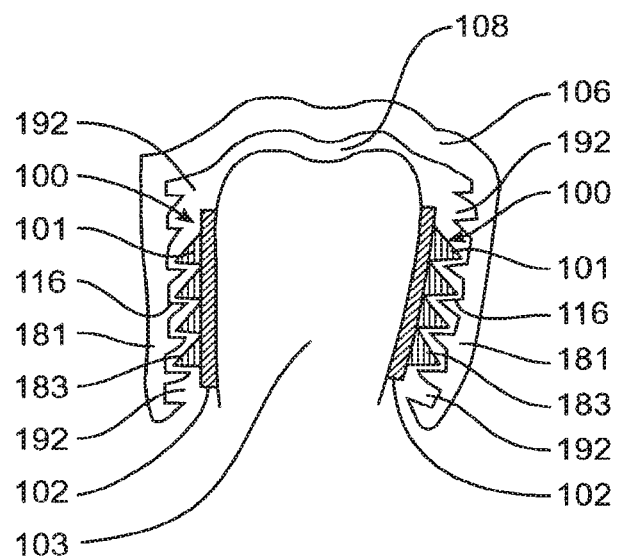
FIGS. 13A-13B illustrate an attachment device and appliance for extruding a tooth in accord with an aspect of the present invention in which engagement between an appliance and attachment are as meshing gears.
Figure 13B:
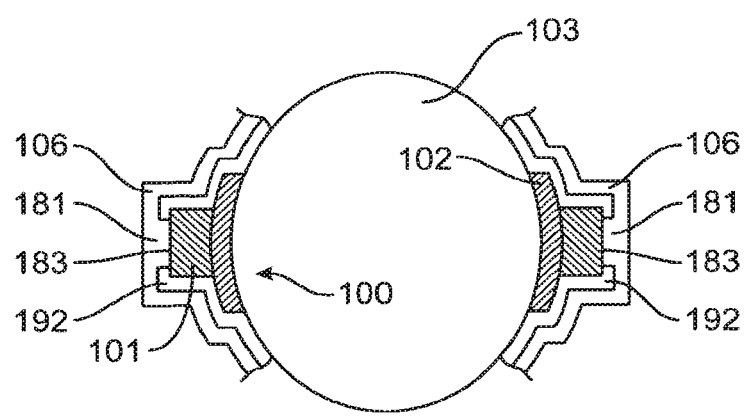

A further embodiment of an attachment device and appliance forming a moving locus of engagement 116 as meshing gears is illustrated with a buccal view in FIG. 13A and an occlusal view in FIG. 13B. A pair of attachment devices 100 is mounted on tooth 103 to extrude tooth 103. An appliance 106 is positioned over tooth 103. Each attachment device 100 includes several teeth 183 for meshing with several teeth 181 of appliance 106. A channel 192 permits relative motion of tooth 103 to appliance 106 over a range of motion and maintains locus of engagement 116 as tooth 103 moves relative to appliance 106 over a substantial range of motion. A space 108 permits tooth 103 to extrude into an intended position.

Figure 14A:
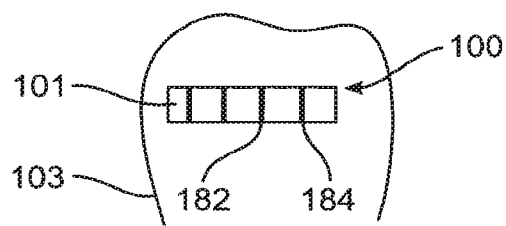
FIGS. 14A-14D illustrate an attachment device and an appliance for rotating a tooth in accord with an embodiment of the present invention in which an appliance as a pawl engages an attachment engaging as a ratchet.
Figure 14B:
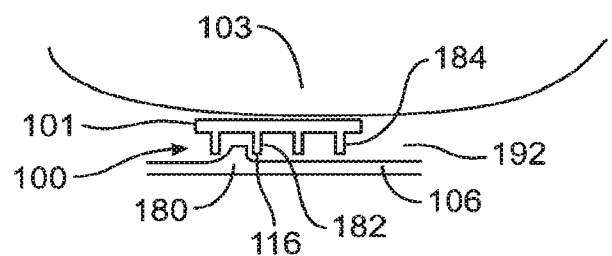
Figure 14C:
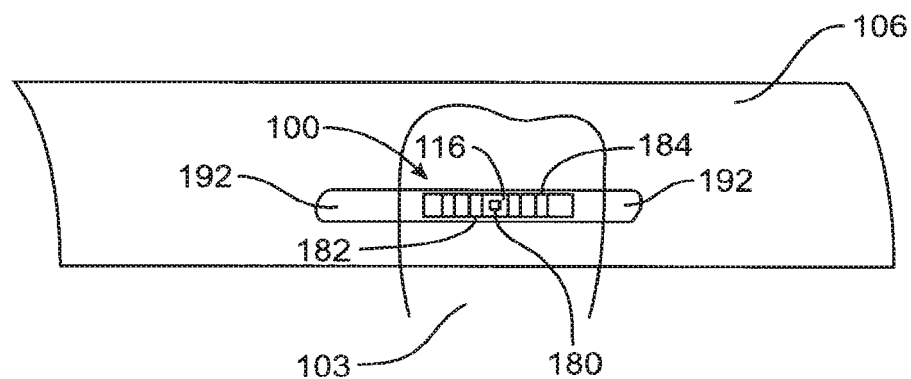
Figure 14D:
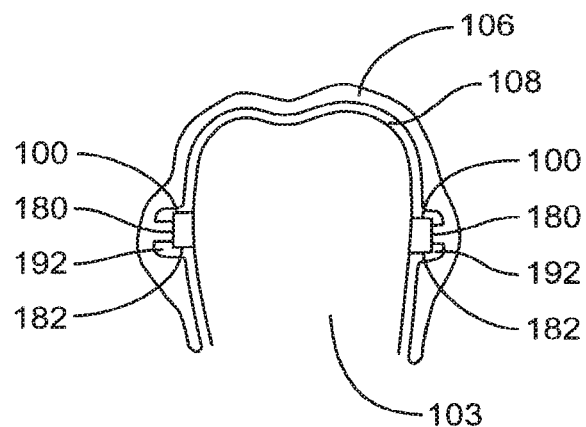

A further embodiment for rotating teeth is illustrated in FIGS. 14A-D. A buccal view of FIG. 14A illustrates a tooth 103 with a bonded attachment 100. Attachment 100 includes a ratchet 182 with several teeth 184. An occlusal view is illustrated in FIG. 14B. Appliance 106 includes a pawl 180 for engaging teeth 184 of ratchet 182. A movable locus of engagement 116 forms as pawl 180 of appliance 106 engages teeth 184 of ratchet 182 of attachment 100. A channel 192 permits relative motion of tooth 103 to appliance 106 over a substantial range of motion. Several teeth 184 of ratchet 182 and channel 192 maintain locus of engagement 116 over a substantial range of motion. A buccal view is illustrated in FIG. 14C and a mesial view in FIG. 14D. Channel 192 formed in appliance 106 extends for several mm beyond teeth 184 of ratchet 182. Pawl 180 engages teeth 184 of ratchet 182 to form movable locus of engagement 116. Locus of engagement 116 is maintained over several mm of motion.

Figure 15:
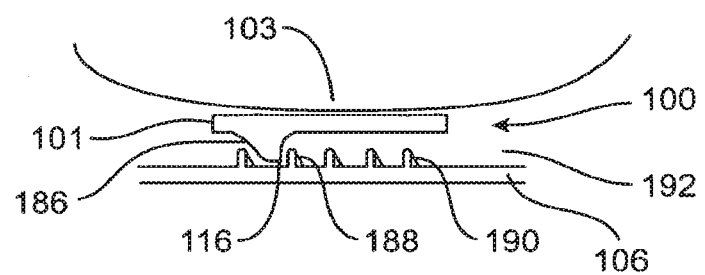
FIG. 15 illustrates an attachment device and an appliance for rotating a tooth in accord with an aspect of the present invention in which an appliance as a ratchet engages an attachment engaging as a pawl.

Another embodiment for rotating teeth with a pawl and ratchet is illustrated in FIG. 15. Attachment 100 includes a pawl 186 formed in attachment body 101. Appliance 106 includes a ratchet 188 comprising several teeth 190 for engaging pawl 186 over a substantial range of motion. A channel 192 formed in appliance 106 permits engagement locus 116 to be maintained over several mm of relative motion of tooth 103 to appliance I 06.

Figure 16:
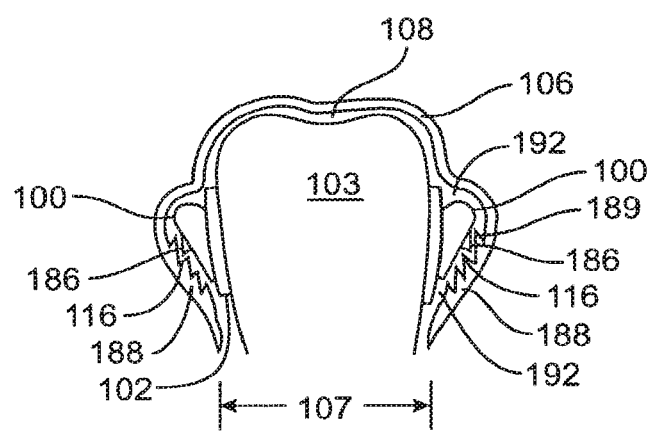
FIG. 16 illustrates a pair of attachment devices as pawls and an appliance as ratchets for extruding a tooth in accord with an aspect of the present invention in which a force of engagement between the pawl and ratchet increases in response to the tooth lagging an intended position during treatment.

A further embodiment illustrated in FIG. 16 includes a pawl 186 of attachment 100 mounted to increasingly engage the teeth 189 of a ratchet 188 of an appliance 106. A space 108 permits a tooth 103 to move into an intended position resulting in extrusion of tooth 103. A channel 192 permits tooth 103 to move relative to appliance 106 over a substantial range of motion. Locus of engagement 116 is maintained over several mm of motion of tooth 103 relative to appliance 106 by several teeth 189 of ratchet 188 and channel 192. Tooth 103 lagging an intended position relative to appliance 106 increases a dimension across 107 appliance 106. This increased dimension deforms and stretches appliance 106 and increases engagement between teeth 189 of ratchet 188 of appliance 106 and pawl 186 of attachment 100. A force of engagement between the force receiving pawl 186 and force transmitting ratchet increases in response to the tooth lagging an intended position during treatment. Motion ceases when an equilibrium is established as described above.

Figure 17A:
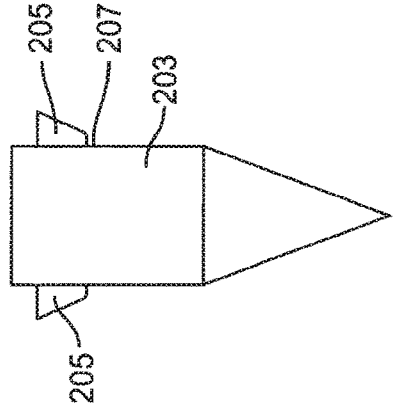
FIGS. 17A-E illustrate a process for forming appliances to engage attachments with increased a force.
Figure 17B:
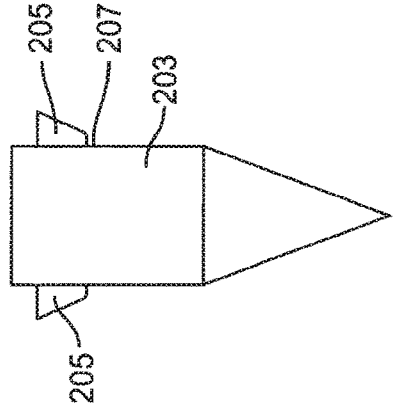
Figure 17C:
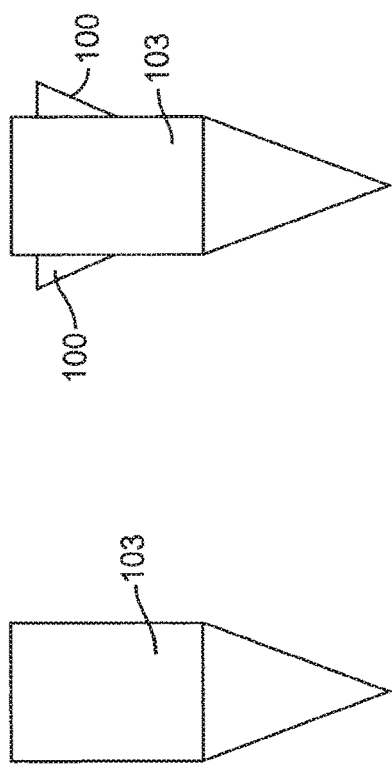
Figure 17D:
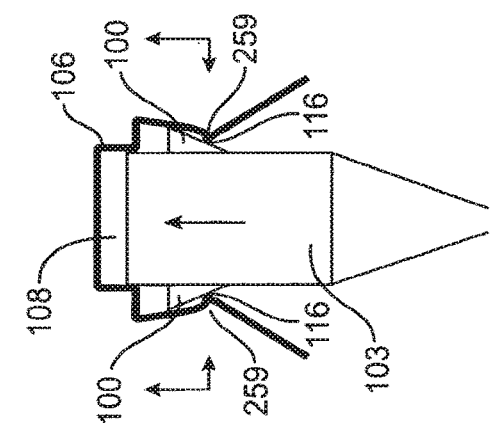
Figure 17E:
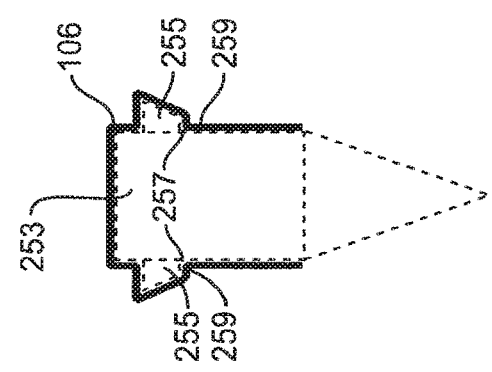

A process for making appliances with increased force transmission to an attachment is illustrated in FIGS. 17A-17E. A tooth 103 is illustrated in FIG. 17A. Tooth 103 has a pair of bonded attachments 100 as illustrated in FIG. 17B. A virtual tooth 203 is made on a computer from a digital data set representing tooth 103 as illustrated in FIG. 17C. Virtual tooth 203 has virtual attachment 205 affixed to it. Virtual attachment 205 is a modified representation of attachment 100. Virtual attachment 100 is modified to produce attachment 205. For example, a notch 207 is formed on an end of the virtual attachment. In alternate embodiments, notch 207 is positioned elsewhere on attachment 100. Notch 207 is also described as a virtual pressure point as the appliance formed over this point will produce increased force on an attachment. Virtual attachment 205 may be enlarged to form a channel and enable a locus of engagement to move over a substantial range. An appliance 106 is formed to fit over positive molds of tooth 253, attachment 255 and notch 257, as illustrated in FIG. 17D. Appliance 106 is positioned over a tooth 103 and attachments 100 and produces locus of engagement 116 as illustrated in FIG. 17E. Locus of engagement 116 is formed at increased prominence 259 of appliance 106. Increased prominence 259 increases stretching of appliance 106 and increases force transmitted from appliance 106 and force received by attachment device 100. Increased prominence 259 is also described as a pressure point.

Figure 18:
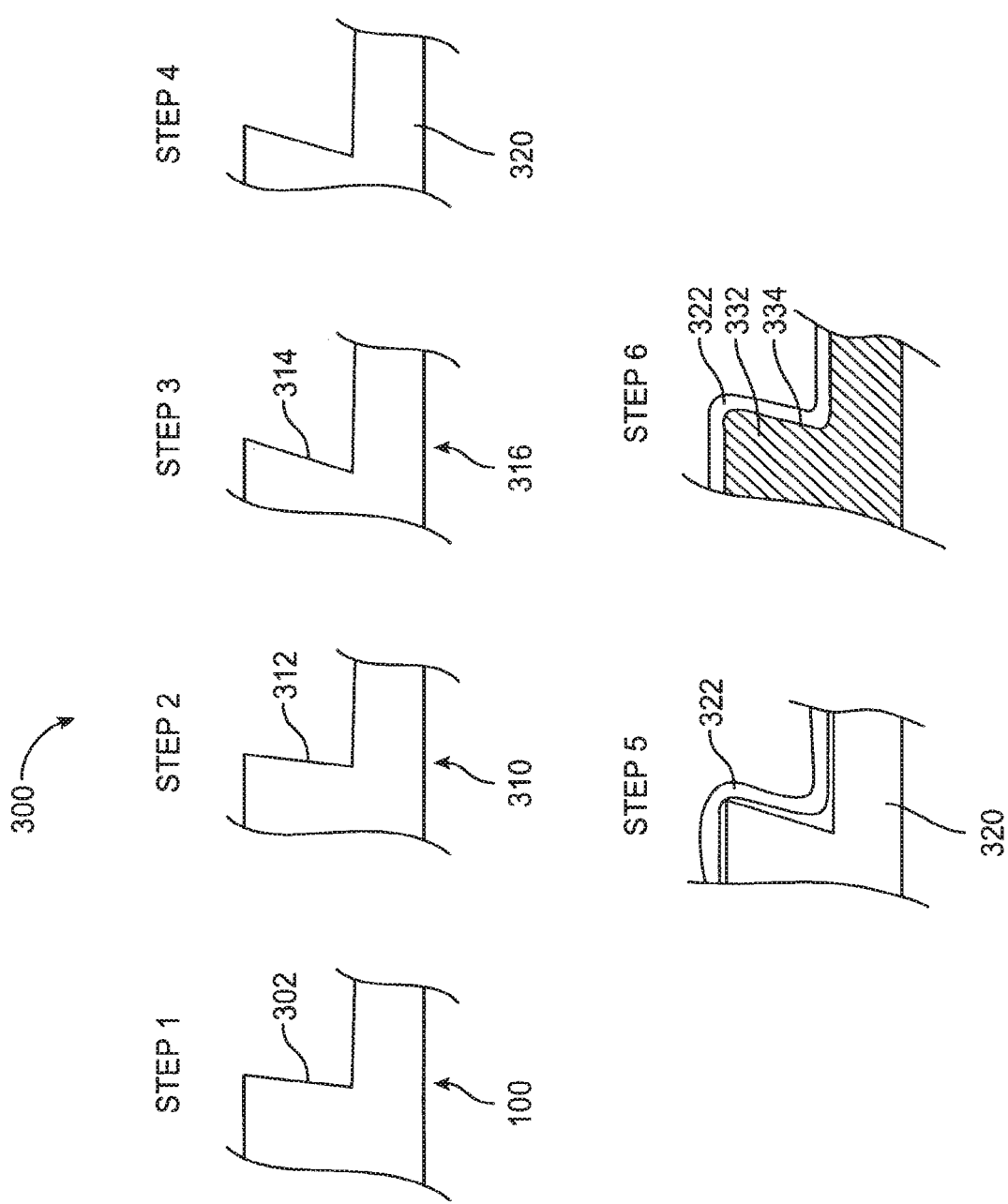
FIG. 18 illustrates an improved process for forming an appliance to fit fine detail of an attachment device.

An improved process 300 for making an attachment 100 having a surface formed to a desired shape is illustrated in FIG. 18. During the formation of an appliance receptacle, the appliance polymer may bridge across corners and other sharp transitions of the mold. This effect is referred to as webbing and is at least partially corrected as illustrated in FIG. 18. A desired shape formed in surface 302 of an attachment 100 is illustrated at STEP 1. A virtual attachment 310 having the desired shape formed in virtual surface 312 is illustrated at STEP 2. Virtual attachment 310 and shaped virtual surface 312 have dimensions matching attachment 100 and desired surface 302. At STEP 3 virtual surface 312 is modified to form modified virtual surface 314 of modified virtual attachment 316. Modified virtual surface 314 has a modified bevel to correct for webbing. A positive mold 320 is formed from modified virtual attachment 316 as illustrated in STEP 4. An appliance 322 is formed from positive mold 320 as illustrated in STEP 5. At STEP 6 an attachment 332 having a surface 334 closely matching desired surface 302 is formed from appliance 322.

Figure 19A:
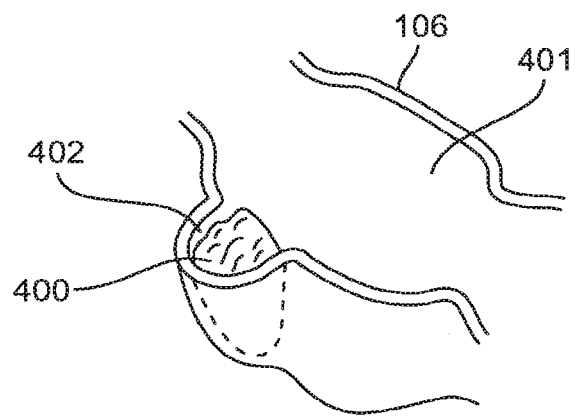
FIGS. 19A-C illustrate a process for forming an attachment in situ on a patient.
Figure 19B:
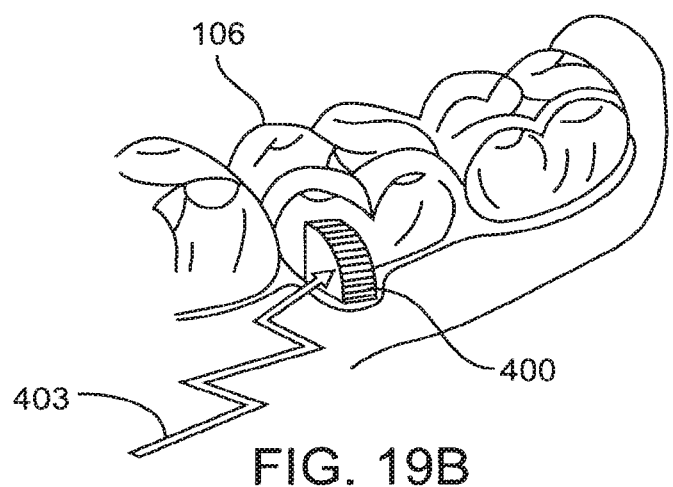
Figure 19C:
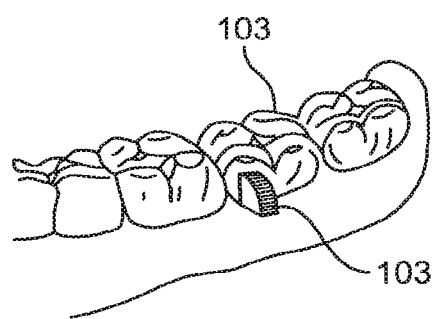

In a preferred embodiment, the attachment is formed in situ on the patient with a polymerizing material. The method of casting with a polymerizing material is similar to the method of basic casting described in U.S. Pat. No. 6,309,215, the full disclosure of which is incorporated herein by reference. In one embodiment, an elastic positioning appliance 106 is formed over a mold 320 of an attachment device 100, as previously depicted in FIG. 18. At this point, a malleable polymerizing material 400 may be placed into the negative impression 402 in an appliance 106. FIG. 19A illustrates an enlarged view of the underside of a portion of the appliance 106, revealing a receiving cavity 401 for a tooth 103 and the negative impression 402 of an attachment device 100 filled with a polymerizing material 400. The appliance 106 is seated in position in the oral cavity, as shown in FIG. 19B. The polymerizing material 400 is in contact with the desired dental surface, in this case a tooth 103, and is positioned in the proper location. The material 400 is polymerized (depicted by jagged arrow 403) by any means, such as an external stimulus. Upon removal of the appliance 106, the formed attachment device 100 remains in place on the tooth 103, as shown in FIG. 19C. Although a specific attachment is shown in FIG. 19C, any suitable attachment as described above can be formed.

Additional details of the attachment forming process are described in U.S. Pat. No. 6,309,215 and in U.S. patent application Ser. No. 10/040,269 filed Oct. 29, 2001 and issued as U.S. Pat. No. 6,705,863, the full disclosures of which are incorporated herein by reference.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for fabricating a teeth repositioning appliance, the method comprising:
receiving a digital representation of: at least one of a patient's teeth, and a modified attachment bonded to a tooth of the at least one of the patient's teeth, said modified attachment having a modified surface shape as compared to a surface shape of an attachment bonded to the tooth;
generating a positive mold of the tooth and the modified attachment for the formation of a tooth repositioning appliance to move the tooth along a path, the positive mold of the tooth and the modified attachment being based on the digital representation of the at least one of the patient's teeth and the modified attachment; and
forming the teeth repositioning appliance over the positive mold,
wherein said teeth repositioning appliance is a polymeric shell repositioning appliance comprising a force-transmitting component structured so that the force-transmitting component engages the modified attachment at a contact point within a locus of engagement to urge the tooth along the path, and wherein a position of the contact point adjusts within the locus of engagement as the tooth is repositioned so that the force transmitted to said tooth increases if the tooth lags an intended position along the path.

2. The method of claim 1, wherein the modified attachment is larger than the attachment so as to form a channel and enable a locus of engagement to move.

3. The method of claim 1, wherein the modified attachment is generated by forming a pressure point on the attachment.

4. The method of claim 3, wherein the pressure point is a notch formed at an end of the attachment.

5. The method of claim 1, wherein the modified attachment is generated by forming a modified bevel on a surface of the attachment.

6. The method of claim 1, wherein the attachment includes a first surface and a second surface at a first angle with respect to one another, and the modified attachment includes a digital representation of the first surface and the second surface at a second angle with respect to one another that is less than the first angle.

7. The method of claim 1, wherein the modified attachment includes the force-receiving component.

* * * * *